United States Patent
Sohn

(10) Patent No.: US 12,304,901 B2
(45) Date of Patent: May 20, 2025

(54) SELECTIVE LIGANDS FOR TAU AGGREGATES

(71) Applicant: Sentonix, Inc., Arlington, MA (US)

(72) Inventor: Daniel Dungan Sohn, Södertälje (SE)

(73) Assignee: Sentonix, Inc., Arlington, MA (US)

( * ) Notice: Subject to any disclaimer, the term of this patent is extended or adjusted under 35 U.S.C. 154(b) by 0 days.

(21) Appl. No.: 18/929,263

(22) Filed: Oct. 28, 2024

(65) Prior Publication Data

US 2025/0066330 A1 Feb. 27, 2025

Related U.S. Application Data

(63) Continuation of application No. PCT/EP2023/080605, filed on Nov. 2, 2023.

(30) Foreign Application Priority Data

| Nov. 3, 2022 | (GB) | 2216351.3 |
| Aug. 17, 2023 | (GB) | 2312590.9 |

(51) Int. Cl.
| C07D 401/14 | (2006.01) |
| A61K 31/4545 | (2006.01) |
| A61K 51/04 | (2006.01) |
| C07B 59/00 | (2006.01) |

(52) U.S. Cl.
CPC ........ *C07D 401/14* (2013.01); *A61K 31/4545* (2013.01); *A61K 51/0455* (2013.01); *C07B 59/002* (2013.01)

(58) Field of Classification Search
CPC .................................................. C07D 401/14
USPC ....................................................... 514/318
See application file for complete search history.

(56) References Cited

U.S. PATENT DOCUMENTS

2012/0302755 A1    11/2012   Chen et al.

FOREIGN PATENT DOCUMENTS

| DE | 3722992 A1 | 1/1989 |
| WO | WO-2006044503 A2 | 4/2006 |
| WO | WO-2006080821 A1 | 8/2006 |
| WO | WO-2007086800 A1 | 8/2007 |
| WO | WO-2012164071 A1 | 12/2012 |
| WO | WO-2014140592 A1 | 9/2014 |
| WO | WO-2015110263 A1 | 7/2015 |
| WO | WO-2017009454 A1 | 1/2017 |
| WO | WO-2017153601 A1 | 9/2017 |
| WO | WO-2019025595 A1 | 2/2019 |
| WO | WO-2019049061 A1 | 3/2019 |
| WO | WO-2019197502 A1 | 10/2019 |
| WO | 2021074351 * | 4/2021 |
| WO | WO-2021074351 A1 * | 4/2021 | ......... A61K 51/0455 |
| WO | WO-2024094816 A1 | 5/2024 |

OTHER PUBLICATIONS

Åslund, A., et al., "Novel pentameric thiophene derivatives for in vitro and in vivo optical imaging of a plethora of protein aggregates in cerebral amyloidoses," ACS Chem. Biol. 4(8):673-684, ACS Publications, United States (Aug. 2009).

Arendt, T., et al., "Tau and tauopathies," Brain Research Bulletin 126(Pt 3):238-292, Elsevier, Netherlands (Sep. 2016).

Bäck, M., et al., "Anionic Oligothiophenes Compete for Binding of X-34 but not PIB to Recombinant Aβ Amyloid Fibrils and Alzheimer's Disease Brain-Derived Aβ," Chemistry 22(51):18335-18338, Wiley, United States (Dec. 2016).

Ballatore, C., "Tau-mediated neurodegeneration in Alzheimer's disease and related disorders," Nat Rev Neurosci. 8(9):663-672, Nature Portfolio, Germany (Sep. 2007).

Biernat, J., et al., "The switch of tau protein to an Alzheimer-like state includes the phosphorylation of two serine-proline motifs upstream of the microtubule binding region," EMBO J. 11(4):1593-1597, EMBO Press, Germany (Apr. 1992).

Cesura, A.M., et al., "Characterization of the binding of [3H]Ro 41-1049 to the active site of human monoamine oxidase-A," Mol. Phamacol. 37(3):358-366, The American Society for Pharmacology and Experimental Therapeutics, United States (Mar. 1990).

Clavaguera, F., et al., "Brain homogenates from human tauopathies induce tau inclusions in mouse brain," Proc. Natl. Acad. Sci. 110(23):9535-9540, National Academy of Sciences, United States (Jun. 2013).

Database Registry [Online] Chemical Abstracts Service, "XP002791969," accessed on May 21, 2019, 1 page.

Database Registry [Online] Chemical Abstracts Service, "XP002791970," accessed on May 21, 2019, 1 page.

Database Registry [Online] Chemical Abstracts Service, "XP002791971," accessed on May 21, 2019, 1 page.

Enamine Advanced HTS Collection Catalogue, "Compound with CAS Registry No. 930868-12-5," Chemcats Abstract Accession No. 1472294918, accessed in Jun. 2019, 1 page.

Fodero-Tavoletti, M.T., et al., "18F-THK523: a novel in vivo tau imaging ligand for Alzheimer's disease," Brain 134(Pt 4):1089-1100, Oxford University Press, United Kingdom (Apr. 2011).

Gleave, R.J., et al., "Synthesis and evaluation of 3-amino-6-arylpyridazines as selective CB(2) agonists for the treatment of inflammatory pain," Bioorganic & Medicinal Chemistry Letters 20(2):465-468, Elsevier, Netherlands (Jan. 2010).

(Continued)

*Primary Examiner* — Niloofar Rahmani
(74) *Attorney, Agent, or Firm* — Sterne, Kessler, Goldstein & Fox P.L.L.C.

(57) ABSTRACT

The invention provides a compound of formula (I), or a pharmaceutically acceptable salt, ester or carbamate thereof, or a salt of such an ester or carbamate, (I)

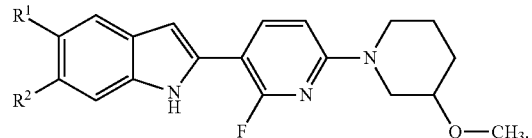

18 Claims, 1 Drawing Sheet

(56) References Cited

OTHER PUBLICATIONS

Hashimoto, H., et al., "Radiosynthesis, photoisomerization, biodistribution, and metabolite analysis of 11C-PBB3 as a clinically useful PET probe for imaging of tau pathology," J Nucl Med 55(9):1532-1538, Society of Nuclear Medicine and Molecular Imaging, United States (Sep. 2014).

Hostetler, E.D., et al., "Preclinical Characterization of 18F-MK-6240, a Promising PET Tracer for In Vivo Quantification of Human Neurofibrillary Tangles," J Nucl Med 57(10):1599-1606, Society of Nuclear Medicine and Molecular Imaging, United States (Oct. 2016).

International Search Report and Written Opinion for International Application No. PCT/EP2019/059165, European Patent Office, Netherlands, mailed on Jul. 10, 2019, 29 pages.

International Search Report and Written Opinion for International Application No. PCT/EP2020/079139, European Patent Office, Netherlands, mailed on Feb. 1, 2021, 16 pages.

Johnson, A.E., et al., "AZD2184: a radioligand for sensitive detection of beta-amyloid deposits," Journal of Neurochemistry 108(5):1177-1186, Wiley, United States (Mar. 2009).

Jureus, A., et al., "Characterization of AZD4694, a novel fluorinated Abeta plaque neuroimaging PET radioligand," Journal of Neurochemistry 114(3):784-794, Wiley, United States (Aug. 2010).

Klingstedt, T., et al., "Synthesis of a library of oligothiophenes and their utilization as fluorescent ligands for spectral assignment of protein aggregates," Org. Biomol. Chem. 9(24):8356-8370, Royal Society of Chemistry, United Kingdom (Dec. 2011).

Klingstedt, T., et al., "The Structural Basis for Optimal Performance of Oligothiophene-Based Fluorescent Amyloid Ligands: Conformational Flexibility is Essential for Spectral Assignment of a Diversity of Protein Aggregates," Chemistry 19(31): 10179-10192, Wiley, United States (Jul. 2013).

Klingstedt, T., et al., "Distinct Spacing Between Anionic Groups: An Essential Chemical Determinant for Achieving Thiophene-Based Ligands to Distinguish β-Amyloid or Tau Polymorphic Aggregates," Chemistry 21(25):9072-9082, Wiley, United States (Jun. 2015).

Klunk, W.E., et al., "Imaging brain amyloid in Alzheimer's disease with Pittsburgh Compound-B," Ann. Neurol. 55(3):306-319, Wiley, United States (Mar. 2004).

Kudo, Y., et al., "2-(2-[2-Dimethylaminothiazol-5-yl]ethenyl)-6-(2-[fluoro]ethoxy)benzoxazole: a novel PET agent for in vivo detection of dense amyloid plaques in Alzheimer's disease patients," J. Nucl. Med. 48(4):553-561, Society of Nuclear Medicine and Molecular Imaging, United States (Apr. 2007).

Levine, H., and Walker, L.C., "Molecular polymorphism of Abeta in Alzheimer's disease," Neurobiol. Aging 31(4):542-548, Elsevier, Netherlands (Aug. 2010).

Li, C., and Götz, J., "Tau-based therapies in neurodegeneration: opportunities and challenges," Nat Rev Drug Discov 16(12):863-883, Nature Portfolio, Germany (Dec. 2017).

Lu, J.X., et al., "Molecular structure of β-amyloid fibrils in Alzheimer's disease brain tissue," Cell 154(6):1257-1268, Cell Press, United States (Sep. 2013).

Maarouf, C.L., et al., "Histopathological and molecular heterogeneity among individuals with dementia associated with Presenilin mutations," Mol Neurodegener 3:20, BioMed Central, United Kingdom (Nov. 2008).

Maruyama, M., et al., "Imaging of tau pathology in a tauopathy mouse model and in Alzheimer patients compared to normal controls," Neuron 79(6):1094-1108, Cell Press, United States (Sep. 2013).

Morozova, O.A., "Conformational features of tau fibrils from Alzheimer's disease brain are faithfully propagated by unmodified recombinant protein," Biochemistry 52(40):6960-6967, ACS Publications, United States (Oct. 2013).

Mullard, A., "Pharma pumps up anti-tau Alzheimer pipeline despite first Phase III failure," Nature Reviews Drug Discovery 15(9):591-592, Nature Portfolio, Germany (Aug. 2016).

Murugan, N.A., et al., "Cross-interaction of tau PET tracers with monoamine oxidase B: evidence from in silico modelling and in vivo imaging," European journal of nuclear medicine and molecular imaging 46(6):1369-1382, Springer Nature, Germany (Jun. 2019).

Nilsson, K.P.R., "Small organic probes as amyloid specific ligands—past and recent molecular scaffolds," FEBS Lett. 583(16):2593-2599, Wiley, United States (Aug. 2009).

Qiang, W., et al., "Structural variation in amyloid-β fibrils from Alzheimer's disease clinical subtypes," Nature 541(7636):217-221, Nature Portfolio, Germany (Jan. 2017).

Ross, C.A., and Poirier, M.A., "Protein aggregation and neurodegenerative disease," Nat. Med. 10 Suppl:S10-7, Nature Portfolio, Germany (Jul. 2004).

Saint-Aubert, L., et al., "Tau PET imaging: present and future directions," Molecular Neurodegeneration 12(1):19, BioMed Central, United Kingdom (Feb. 2017).

Shirani, H., et al., "A Palette of Fluorescent Thiophene-Based Ligands for the Identification of Protein Aggregates," Chemistry 21(43):15133-15137, Wiley, United States (Oct. 2015).

Shirani, H., et al., "Synthesis of Thiophene-Based Optical Ligands That Selectively Detect Tau Pathology in Alzheimer's Disease," Chem. Eur. J. 23(67):17127-17135, Wiley, United States (Dec. 2017).

Small, G.W., et al., "PET of brain amyloid and tau in mild cognitive impairment," N. Eng. J. Med. 355(25):2652-2663, Massachusetts Medical Society, United States (Dec. 2006).

Taghavi, A., et al., "N'-benzylidene-benzohydrazides as novel and selective tau-PHF ligands," Alzheimers Dis. 27(4):835-843, Sage Publishing, United States (2011).

Tsugeno, Y., et al., "Regions of the molecule responsible for substrate specificity of monoamine oxidase A and B: a chimeric enzyme analysis," J Biochem 118(5):974-980, Oxford University Press, United Kingdom (Nov. 1995).

United Kingdom Search for GB Application No. 1806004.6, United Kingdom Intellectual Property Office, United Kingdom, mailed on Dec. 10, 2018, 5 pages.

United Kingdom Search for GB Application No. 1914989.7, United Kingdom Intellectual Property Office, United Kingdom, mailed on Apr. 9, 2020, 2 pages.

Weyler, W., and Salach, J.I., "Purification and properties of mitochondrial monoamine oxidase type A from human placenta," J. Biol. Chem. 260(24):13199-13207, Elsevier, Netherlands (Oct. 1985).

Written Opinion for International Application No. PCT/EP2023/080605, European Patent Office, Germany, mailed on Oct. 5, 2024, 7 pages.

Xia, C.F., et al., "[(18)F]T807, a novel tau positron emission tomography imaging agent for Alzheimer's disease," Alzheimers Dement 9(6):666-676, Wiley, United States (Nov. 2013).

Yang, L., et al., "Brain amyloid imaging—FDA approval of florbetapir F18 injection," N. Engl. J. Med. 367(10):885-887, Massachusetts Medical Society, United States (Sep. 2012).

Zhang, W., et al., "A highly selective and specific PET tracer for imaging of tau pathologies," Alzheimers Dis. 31(3):601-612, Sage Publishing, United States (2012).

\* cited by examiner

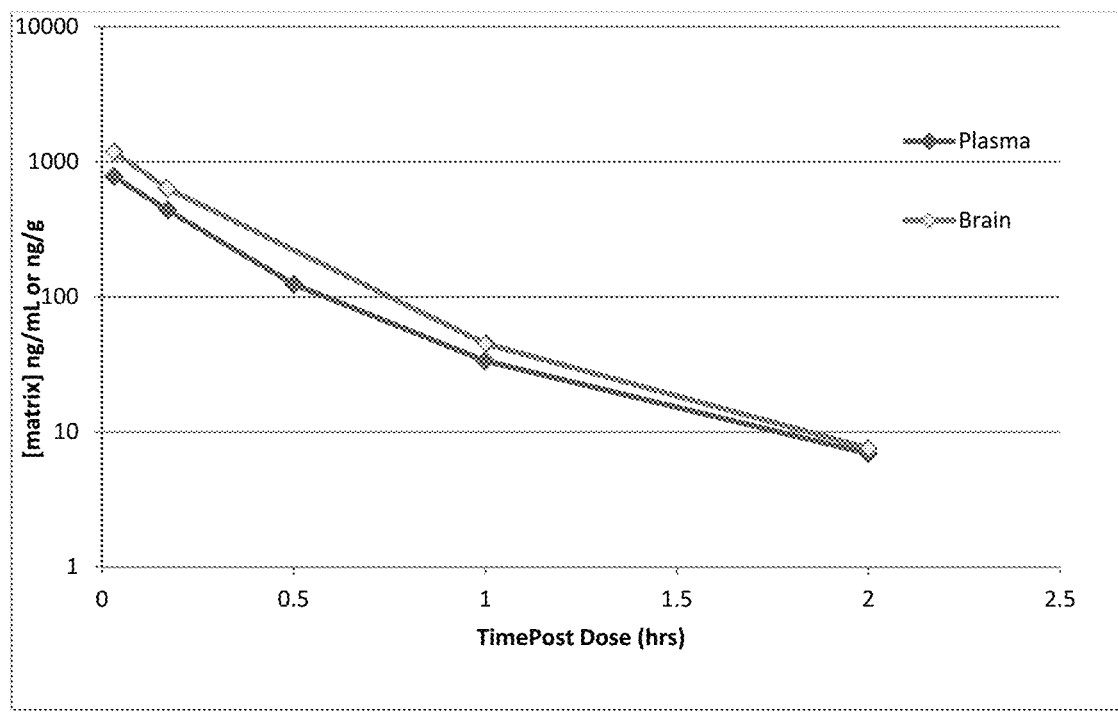

SELECTIVE LIGANDS FOR TAU AGGREGATES

CROSS REFERENCE TO EARLIER FILED APPLICATIONS

The present application is a Continuation application of PCT Application No. PCT/EP2023/080605, filed Nov. 2, 2023, which claims priority to GB 2216351.3, filed Nov. 3, 2022, and GB 2312590.9, filed Aug. 17, 2023, each of which is incorporated herein by reference in its entirety.

FIELD OF THE INVENTION

The present invention relates to compounds of formula (I) and compositions comprising compounds of formula (I). The compounds of the present invention are useful in the diagnosis and treatment of neurodegenerative diseases, and especially tauopathies such as Alzheimer's disease.

INTRODUCTION

Alzheimer's disease is a neurodegenerative disorder causing symptoms that include memory loss, difficulties with thinking, problem-solving, speech and/or language, personality changes, hallucinations, delusions, low mood and anxiety. It is the most common cause of dementia. Alzheimer's is a progressive disease and over time more symptoms develop, and the symptoms become more severe.

Protein deposits are the pathological hallmarks of a wide range of neurodegenerative diseases (C. A. Ross, M. A. Poirier, Nat. Med. 2004, 10, 10-17), including Alzheimer's disease and corticobasal degeneration. Small hydrophobic ligands that are selective for protein aggregates having an extensive cross β-pleated sheet conformation and sufficient structural regularity have been developed. The most common ligands are derivatives of Congo Red or thioflavins and a variety of other molecular scaffolds have also been reported (K. P. R. Nilsson, FEBS Lett. 2009, 583, 2593-2599). However, most of these ligands can only generally detect disease-associated protein aggregates, and they are not able to detect specific disease-associated protein aggregates consisting of a distinct protein.

The microtubule associated protein tau is one protein deposit shown to cause neurodegeneration. Tau can form intracellular fibrillary deposits in neurons and glial cells, and these tau deposits are linked to a large variety of disorders, collectively referred to as tauopathies. Tauopathies include more than 20 disorders including Alzheimer's disease, progressive supranuclear palsy (PSP), corticobasal degeneration (CBD), and Pick's disease. Although dysfunction of tau has unequivocally been shown to be able to cause neurodegeneration, the precise mechanisms of how tau is involved in neurodegenerative disorders is still poorly understood. According to currently emerging cell biological concepts, tau might play a role in the regulation of neuronal plasticity in a wide array of neuronal networks. In addition, it might be involved in regulating genome stability (Arendt, T., et al, Brain Research Bulletin, 2016, 126, 238-292).

In Alzheimer's disease, the two major proteinaceous deposits are extracellular senile plaques consisting of aggregated amyloid-β (Aβ) peptide and intraneuronal neurofibrillary tangles (NFTs) composed of aggregated tau (C. A. Ross, M. A. Poirier, Nat. Med. 2004, 10, 10-17; C. Ballatore, V. M. Y Lee, J. Q. Trojanowski. Nat Rev Neurosci. 2007, 8, 663-672). The development of ligands that can specifically target Aβ or tau deposits are essential for clinical diagnostic of Alzheimer's disease, as well as for evaluating the contribution of these respective aggregated species to the complex molecular pathology in Alzheimer's disease brain. Molecular scaffolds enabling visualization of Aβ deposits in humans with Alzheimer's disease by positron emission tomography (PET) imaging have been presented (W. E. Klunk, et al, Ann. Neurol. 2004, 55, 306-319; Y. Kudo, et al, J. Nucl. Med. 2007, 48, 553-561; and L. Yang, D., et al, N. Engl. J. Med. 2012, 367, 885-887). More recently, some molecular scaffolds targeting the other pathological hallmark in Alzheimer's disease, tau deposits, have also been recognized (G. W. Small, et al, N. Eng. J. Med. 2006, 355, 2652-2663; Taghavi, et al, Alzheimers Dis. 2011, 27, 835-843; M. T. Fodero-Tavoletti, et al, Brain. 2011, 134, 1089-1100; W. Zhang, et al, Alzheimers Dis. 2012, 31, 601-612; M. Maruyama, et al, Neuron 2013, 79, 1094-1108; and C. F. Xia, et al. Alzheimers Dement. 2013, 9, 666-676).

Luminescent conjugated oligothiophenes (LCOs) have been utilized for fluorescence imaging of protein aggregates. Compared to conventional ligands, LCOs have been shown to detect a wider range of disease-associated protein aggregates (A. Aslund, et al, ACS Chem. Biol. 2009, 4, 673-684; T. Klingstedt, et al, Org. Biomol. Chem. 2011, 9, 8356-8370; H. Shirani, et al, Chemistry 2015, 21, 15133-15137). In addition, LCOs having distinct chemical compositions can be utilized for spectral assessment of distinct protein aggregates, such as Aβ or tau deposits in Alzheimer's disease (T. Klingstedt, et al, Chemistry 2013, 19, 10179-1019; T. Klingstedt, et al, Chemistry 2015, 21, 9072-9082). Lately, a thiophene based tetrameric ligand, q-FTAA-CN with a strikingly higher affinity for Aβ deposits than aggregated species composed of tau was identified (M. Bäck, et al, Chemistry. 2016, 22, 18335-18338).

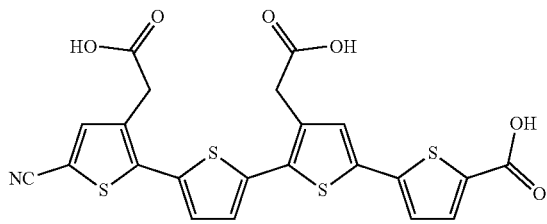

q-FTAA-CN

PBB3 is also known to be a tau specific ligand (M. Maruyama, et al, Neuron 2013, 79, 1094-1108).

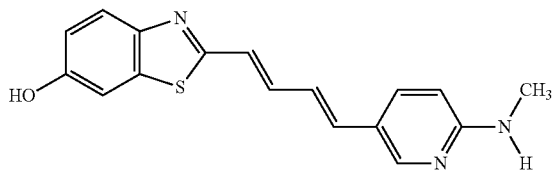

PBB3

MK6240 is also known to be a tau specific ligand (E. D. Hostetler, et al, *J Nucl Med* 2016, 57, 1599-1606).

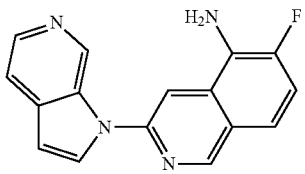

MK-6240

However, different morphotypes of AR and tau aggregates have been reported (C. L. Maarouf, let al, *Mol. Neurodegener.* 2008, 3, 20; H. Levine, L. C. Walker, *Neurobiol. Aging* 2010, 31, 542-548; F. Clavaguera, et al, *Proc. Natl. Acad. Sci. USA* 2013, 110, 9535-9540; J. X. Lu, et al, *Cell* 2013, 154, 1257-1268; W. Qiang, et al, *Nature.* 2017, 541, 217-221). The existence of distinct aggregate morphotypes has been suggested to explain the heterogeneous phenotype reported for several neurodegenerative protein aggregation diseases. Hence, a variety of ligands will be necessary to achieve an accurate assessment of the diversity of pathological protein deposits present in neurodegenerative diseases, such as Alzheimer's disease. As such, there is a need to develop further small molecular ligands that target specific disease-associated protein aggregates, and in particular further molecular scaffolds enabling visualization of tau deposits, for example in humans with Alzheimer's disease (and other tauopathies).

Further, the known tau specific ligand PBB3 has been reported to have the significant disadvantage of undergoing photoisomerisation when exposed to fluorescent light (Hashimoto, H., et al, J Nucl Med (2014), Vol. 55, No. 9, pages 1532-1538). Hashimoto et al reported that at 1 min after exposure of a sample of $^{11}$C-PBB3 to fluorescent light, the radiochemical purity of $^{11}$C-PBB3 decreased to 77%, and from 10 to 60 min, the radiochemical purity was approximately 50%. Hashimoto et al also reported that the isomer of $^{11}$C-PBB3 that was formed showed much less specific binding to tau in the brain sections of Alzheimer's disease patients. This property makes PBB3 difficult to synthesize, radiolabel, store, and handle. This limits the practicality of using this tau ligand in in vitro experimentation and in vivo acquisitions (Saint-Aubert, L., et al, Molecular Neurodegeneration (2017), Vol. 12, No. 9: *Tau PET imaging: present and future directions*).

SUMMARY OF INVENTION

The invention provides a compound of formula (I), or a pharmaceutically acceptable salt, ester, or carbamate thereof, or a salt of such an ester or carbamate,

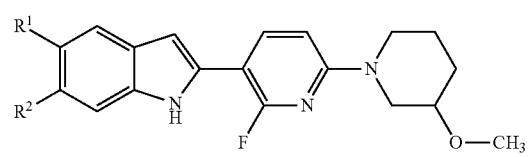

(I)

wherein either:
$R^1$ is OH, and $R^2$ is H; or
$R^1$ is H, and $R^2$ is OH.

The invention also provides a pharmaceutical composition comprising a compound of formula (I), together with a pharmaceutically suitable carrier.

The invention also provides a compound of formula (I), or a composition comprising compound of formula (I), for use as a diagnostic agent, wherein the compound of formula (I) comprises one or more radioisotopes selected from $^{3}$H, $^{1}$C, $^{13}$C, $^{14}$C, $^{13}$N, $^{15}$O, $^{18}$F and $^{19}$F.

The invention also provides the use a compound of formula (I) for the detection of tau deposits.

The invention also provides a compound of formula (I), or a composition comprising compound of formula (I), for use as a diagnostic agent in the diagnosis or monitoring of progression of a disease or disorder selected from the group consisting of Alzheimer's disease, corticobasal degeneration, Pick's disease, progressive supranuclear palsy, Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion-body myositis, chronic traumatic encephalopathy, Down's syndrome, Gerstman-Straussler-Scheinker syndrome, British dementia, familial Danish dementia, dementia pugiiistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.lle383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Straussler-Scheinker with tau, mutations in LRRK2, SLC9A6-related mental retardation, and white matter tauopathy with globular glial inclusions.

The invention also provides a method of diagnosing a patient or monitoring disease progression in a patient comprising administering a compound of formula (I) to the patient, or a composition comprising a compound of formula (I) to the patient.

The invention also provides a compound of formula (I), or a composition comprising a compound of formula (I), for use as a medicament.

BRIEF DESCRIPTION OF THE FIGURE

FIG. 1 shows the concentrations of Example Compound 1 in mouse (NMRI, male, mean n=3 per time point) plasma and brain following IV administration of Example Compound 1 at 1 mg/kg.

DETAILED DESCRIPTION

The compounds of formula (I) (also referred to herein as the compounds of the invention) have excellent binding affinity for tau deposits. The compounds of the invention are also selective tau deposit ligands, i.e. as well as having excellent binding affinity for tau deposits, they also selectively bind tau deposits in preference to amyloid beta (Aβ) deposits.

Furthermore, the compounds of the present invention are not light sensitive, as they do not have a photoisomerisable double bonds in their structure. Therefore, they have significant advantages over the known tau selective ligand PBB3 with respect to their synthesis (including radiolabeling), storage, and handling, and can be feasibly used in in vitro experimentation and in vivo acquisitions.

A further advantage of the compounds of the invention is that the compounds bind to the four-repeat (4R) isomer forms of tau. 4R forms of tau are known to be present in various tauopathies, such as Alzheimer's disease, progressive supranuclear palsy and corticobasal degeneration. This makes the compounds of the invention especially useful for the diagnosis and/or the treatment or prophylaxis of conditions associated with 4R forms of tau, such as Alzheimer's disease, progressive supranuclear palsy and corticobasal degeneration.

A further advantage of the compounds of the invention is that they are expected to have low binding affinity for MAO enzymes in the human brain. As reported in Murugan, N. A., et al, Eur J Nucl Med Mol Imaging. (2019) doi: 10.1007/s00259-019-04305-8, areas of the brain with the highest concentrations of MAO-B overlap with areas of tau pathology in taopathies such as CBD and PSP. Therefore, it is undesirable for a tau deposit ligand to have off-target binding to MAO, as such off-target effects severely limit the use of the tau deposit ligand for in vivo tau imaging. The compounds of the invention are expected to be specific to tau accumulation in the brain, and thus have good specificity and sensitivity when used as tau imaging agent in vivo in all taupathies, including CBD and PSP.

The compounds of the present invention cross the blood-brain barrier to a greater extent than previously disclosed compounds of a similar nature, and also are distributed well across the brain once they have crossed the blood-brain barrier.

Isotopic forms, for example where a hydrogen atom is replaced with deuterium ($^2$H) or tritium ($^3$H), or a carbon atom is replaced with a $^{13}$C atom, or a fluorine atom is replaced with a $^{18}$F atom, are included within the invention. Certain isotopic forms may have beneficial biological properties, for example improved metabolic stability or enhanced therapeutic activity over other isotopic forms. Some specific isotopic forms may be useful for biological imaging purposes, for example carbon-11 ($^{11}$C), nitrogen-13 ($^{13}$N), oxygen-15 ($^{15}$O) or fluorine-18 ($^{18}$F) isotopic variants may be used for positron emission tomography, and tritium (H$^3$) may be used for in vitro studies.

The present invention provides compounds of formula (I):

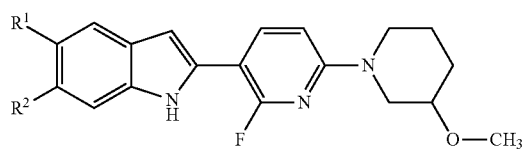

wherein either:

R$^1$ is OH, and R$^2$ is H; or

R$^1$ is H, and R$^2$ is OH.

The compounds of formula (I) can be a compound of formula (Ia) or a compound of formula (Ib):

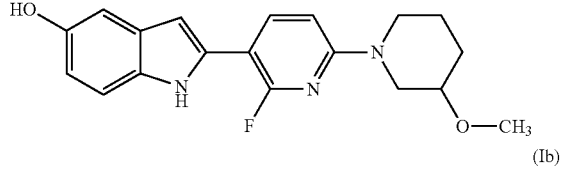

Preferably, the compound of formula (I) has a structural formula selected from the following group:

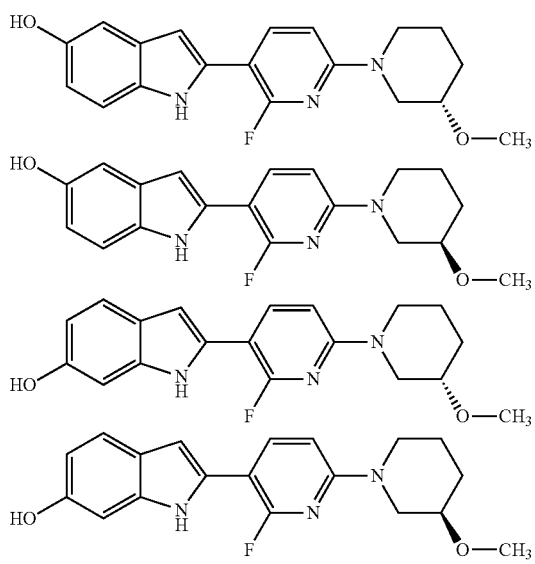

In the compounds of the invention, one or more of the atoms may be an isotope. In the compounds of the invention, one or more of the atoms may be a radiolabeled atom (which may also be referred to as a radioisotope), for example one, two or three of the atoms may be a radiolabeled atom. In particular, one or more of the atoms of R$^1$, R$^2$, the fluoropyridine ring, and/or the —O—CH$_3$ substituent of the piperidine ring may be a radiolabeled atom. A radiolabeled atom may be selected from the group consisting of $^3$H, $^{11}$C, $^{13}$C, $^{14}$C, $^{13}$N, $^{15}$O, $^{18}$F and $^{19}$F, preferably $^3$H, $^{11}$C, $^{14}$C, $^{13}$N, $^{15}$O, $^{18}$F and $^{19}$F, more preferably $^3$H, $^{11}$C, $^{13}$N, 150 and $^{18}$F, even more preferably $^3$H, $^{18}$F and $^{11}$C, and most preferably $^3$H, and $^{18}$F. For example, one or more of the H atoms of R$^1$, R$^2$, the fluoropyridine ring, and/or the —O—CH$_3$ substituent of the piperidine ring may an $^3$H atom, and in particular one or more (for example one, two or three) of the H atoms of the —O—CH$_3$ substituent of the piperidine ring may be an $^3$H atom. Alternatively, or additionally, for example, the F atom of the fluoropyridine ring may be an $^{18}$F or $^{19}$F atom, and preferably a $^{18}$F atom.

The compounds of the invention may form esters, carbamates and/or salts. Salts of compounds of the invention which are suitable for use in medicine are those wherein a counter-ion is pharmaceutically acceptable. However, salts having non-pharmaceutically acceptable counter-ions are within the scope of the present invention, for example, for use as intermediates in the preparation of the compounds of the invention and their pharmaceutically acceptable salts, and physiologically functional derivatives. By the term "physiologically functional derivative" is meant a chemical derivative of a compound of the invention having the same physiological function as the free compound of the invention, for example, by being convertible in the body thereto. Esters and carbamates are examples of physiologically functional derivatives.

Suitable salts according to the invention include those formed with organic or inorganic acids or bases. In particular, suitable salts formed with acids include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, hydroiodic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Compounds of the invention may have an appropriate group converted to an ester or a carbamate. Typical ester and carbamate groups formed from the —OH in the compound of the invention include —OC(O)$R^h$, —OC(O)NH$R^h$, —OC(O)N($R^h$)$_2$ and —OSO$_2$$R^h$, where each $R^h$ is independently selected from the group consisting of $C_{1-8}$alkyl, $C_{2-8}$alkenyl, $C_{2-8}$alkynyl, $C_{3-8}$cycloalkyl and $C_{3-8}$cycloalkyl$C_{1-8}$alkyl, halo$C_{1-8}$alkyl, dihalo$C_{1-8}$alkyl, trihalo$C_{1-8}$alkyl, phenyl and phenyl$C_{1-3}$alkyl; more preferably $R^h$ is selected from the group consisting of $C_{1-6}$alkyl, $C_{2-6}$alkenyl, $C_{2-6}$alkynyl, $C_{3-8}$cycloalkyl and $C_{3-8}$cycloalkyl$C_{1-6}$alkyl.

Those skilled in the art of organic chemistry will appreciate that many organic compounds can form complexes with solvents in which they are reacted or from which they are precipitated or crystallized. These complexes are known as "solvates". For example, a complex with water is known as a hydrate. Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, $2^{nd}$ed. R. Liu, CRC Press, page 553, which are incorporated herein by reference. Accordingly, it will be understood by the skilled person that the compounds of the invention, as well as esters carbamates and/or salts thereof may therefore be present in the form of solvates. Solvates of compounds of the invention which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the compounds of the invention and their pharmaceutically acceptable esters carbamates and/or salts thereof.

A compound which, upon administration to the recipient, is capable of being converted into a compound of the invention as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

Labeled Compounds of the Invention

Compounds of the invention may be labeled. A "label" (which may be a radiolabel or other detectable label, or a tag, marker, detectable marker, tracer, radiotracer or equivalent) is any atom or group suitable for imaging and/or assaying (for example, identifying, imaging, diagnosing, evaluating, detecting and/or quantitating) in vivo or in vitro, and in particular imaging and diagnosing. Suitable labels include, for example, radioisotopes (which may also be referred to as "radiolabeled atoms"), radionuclides, isotopes, positron emitters, gamma emitters, fluorescent groups, luminescent groups, chromogenic groups, biotin (in conjunction with streptavidin complexation) or photoaffinity groups. The type of label chosen will depend on the desired detection method. The position at which the label is integrated or attached to the compounds of the invention is not particularly limited.

Examples of isotopes (such as radioisotopes, radionuclides, positron emitters and gamma emitters) which may be used to label compounds of the invention, include but are not limited to: $^2$H, $^3$H, $^{11}$C, $^{13}$C, $^{14}$C, $^{13}$N, 15O, $^{18}$F and $^{19}$F; preferably $^2$H, $^3$H, $^{11}$C, $^{13}$N, 15O and $^{18}$F; more preferably $^3$H, $^{11}$C, $^{13}$N, $^{15}$O and $^{18}$F; even more preferably $^3$H, $^{11}$C, and $^{18}$F; and most preferably $^3$H and $^{18}$F.

Preferred examples of labeled compounds of the invention are compounds of formula (I) which have a structural formula selected from the following group:

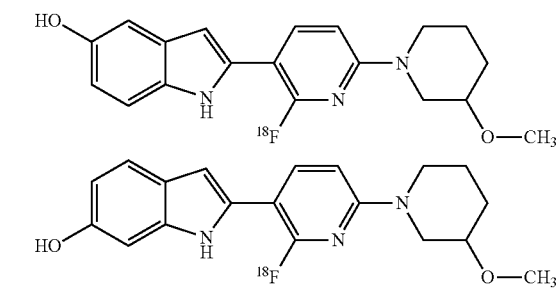

Even more preferred examples of labeled compounds of the invention are compounds of formula (I) which have a structural formula selected from the following group:

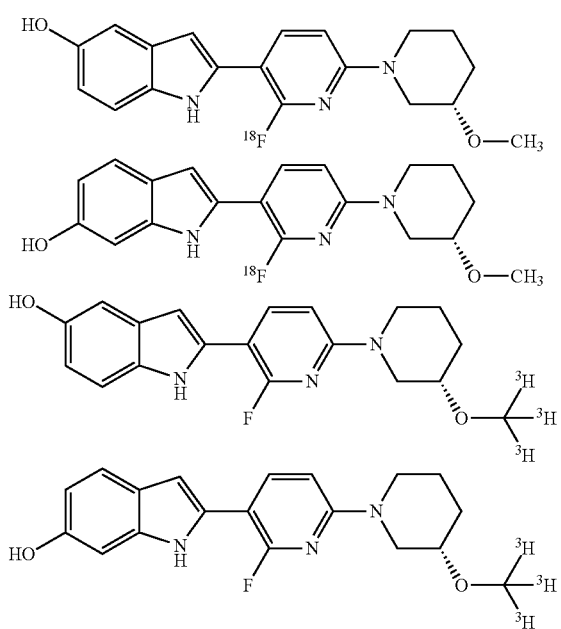

Particularly preferred examples of labeled compounds of the invention are compounds of formula (I) which have a structural formula selected from the following group:

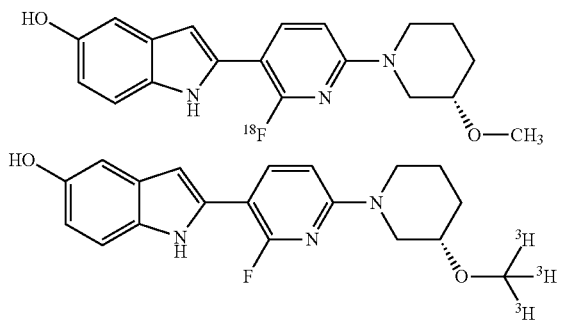

Isotopic form (which also may be referred to as "isotopic variants") of the compounds of the invention can generally be prepared by conventional procedures such as by the methods described in the Examples section using appropriate isotopic variations of suitable reagents that are commercially available or prepared by known synthetic techniques. Radioisotopes, radionuclides, positron emitters and gamma emitters can be included into the compounds of the invention by methods which are routine in the field of organic chemistry. For example, they may be introduced by using a correspondingly labeled starting material when the desired compound of the invention is prepared. Illustrative methods of introducing detectable labels are described, for instance, in US 2012/0302755.

In certain preferred embodiments, compounds of the invention are labeled. In the compounds of the invention, one or more H, one or more C, one or more N, one or more O, and/or the F may be replaced with a $^3$H; $^{11}$C, $^{13}$C or $^{14}$C; $^{13}$N; $^{15}$O; $^{18}$F or $^{19}$F, respectively. Preferably one or more H, one or more C, one or more N, one or more O, and/or the F may be replaced with a $^3$H; $^{11}$C or $^{14}$C; $^{13}$N; $^{15}$O; $^{18}$F or $^{19}$F, respectively; and more preferably $^3$H, $^{11}$C, $^{13}$N, $^{15}$O and $^{18}$F, respectively. Even more preferably one or more H, one or more C, and/or the F may be replaced with a $^3$H, $^{11}$C, and $^{18}$F, respectively. Even more preferably one or more H and/or the F may be replaced with a $^3$H and $^{18}$F, respectively. $^{11}$C, $^{13}$N, $^{15}$O and $^{18}$F are radioactive isotopes. They decay mainly by positron emission. Therefore, the inclusion of such atoms in a compound of the invention makes the compound detectable by positron emission tomography. As such, compounds of the invention comprising one or more $^{11}$C, $^{13}$N, $^{15}$O or $^{18}$F are especially useful as a radioactive tracers, also referred to as a radioactive ligands, for positron emission tomography (PET).

In the compounds of the invention, one or more H may be replaced with a $^3$H radioactive isotope. The inclusion of such an atom in a compound of the invention makes the compound detectable by autoradiography or liquid scintillation counting. Compounds of the invention comprising one or more $^3$H are especially useful as a radioactive tracers for in vitro studies.

In certain preferred embodiments, labeled compounds of the invention may be labeled so that they may be detected in vivo using in vivo magnetic resonance spectroscopy (MRS), magnetic resonance imaging, PET, single-photon SPECT and combinations thereof. For example, a compound of the invention may be labeled with $^{19}$F or $^{13}$C for MRS/MRI; or may be radiolabeled with $C^{11}$, $N^{13}$, $O^{15}$ or $F^{18}$ for PET imaging. Preferably the compounds of the invention comprise one or more radioisotopes selected from $C^{11}$, $N^{13}$, $O^{15}$ and $F^{18}$.

The compounds of the invention comprise a number of C atoms. One or more C in a compound of the invention may be replaced with a $^{11}$C. For example, one C is replaced with one $^1$C; or two C are replaced with two $^{11}$C; or three C are replaced with three $^{11}$C. In certain preferred embodiments, one C is replaced with one $^{11}$C.

The compounds of the invention comprise three N atoms. One or more N in a compound of the invention may be replaced with a $^{13}$N. For example, one N is replaced with a $^{13}$N; or two N are replaced with two $^{13}$N; or three N are replaced with three $^{13}$N. In certain preferred embodiments, one N is replaced with a $^{13}$N.

The compounds of the invention comprise two 0 atoms. One or more 0 in the compound may be replaced with an $^{15}$O. For example, one 0 is replaced with an $^{15}$O; or (two O are replaced with two $^{15}$O. In certain preferred embodiments one 0 is replaced with an $^{15}$O.

The compounds of the invention comprise a number of H atoms. One or more H in a compound of the invention may be replaced with a $^3$H. For example, one H is replaced with one 3H; or two H are replaced with two $^3$H; or three H are replaced with three $^3$H, or at least three H are replaced with at least three $^3$H. In certain preferred embodiments one H is replaced with one $^3$H; or two H are replaced with two $^3$H; or three H are replaced with three $^3$H; for example three H are replaced with three $^3$H.

The compounds of the invention comprise a F atom. In certain preferred embodiments, the F atom in a compound of the invention is replaced with a $F^{18}$.

Uses of Compounds of the Invention

The present invention provides compounds that are selective tau deposit/aggregate ligands. The terms "tau deposit ligand" and "tau aggregate ligand" as used herein are intended to cover any moiety which binds to a tau deposit (a tau deposit may also be referred to as a tau aggregate). For example, the compounds of the invention may bind to one or more of: pathologically aggregated tau, hyperphosphorylated tau, neurofibrillary tangles, paired helical filaments, straight filaments, neurotoxic soluble oligomers, polymers and fibrils. The compounds of the invention are particularly suitable for binding to various types of tau deposits (i.e. tau aggregates). In particular, the compounds of the invention are suitable for binding to tau deposits comprising 4R isomer forms of tau (i.e. tau aggregates comprising 4R isomer forms of tau).

Preferred compounds of the invention have excellent binding affinity for tau deposits. For example, preferably compounds of the invention have an $IC_{50}$ value for tau deposits in a competitive binding assay that is less than 100 nM, preferably less than 70 nM, preferably less than 60 nM, more preferably less than 55 nM, more preferably less than 50 nM, more preferably less than 40 nM, more preferably less than 30 nM, more preferably less than 25 nM, more preferably less than 20 nM, and even more preferably less than 15 nM, for example less than 13 nM, less than 10 nM, less than 8 nM, less than 6 nM, less than 5 nM, less than 4 nM, less than 3 nM, or less than 2 nM. In one preferred embodiment, compounds of the invention have an $IC_{50}$ value for tau deposits of less than 70 nM in a competitive binding assay. In another preferred embodiment, compounds of the invention have an $IC_{50}$ value for tau deposits of less than 50 nM in a competitive binding assay. In another preferred embodiment, compounds of the invention have an $IC_{50}$ value for tau deposits of less than 30 nM in a competitive binding assay. In another preferred embodiment, compounds of the invention have an $IC_{50}$ value for tau deposits of less than 20 nM in a competitive binding assay. In another preferred embodiment, compounds of the invention have an $IC_{50}$ value for tau deposits of less than 15 nM in a competitive binding assay. In another preferred embodiment, compounds of the invention have an $IC_{50}$ value for tau deposits of less than 10 nM in a competitive binding assay. In another preferred embodiment, compounds of the invention have an $IC_{50}$ value for tau deposits of less than 5 nM in a competitive binding assay. In another preferred embodiment, compounds of the invention have an $IC_{50}$ value for tau deposits of less than 3 nM in a competitive binding assay. It is especially preferred that compounds of the invention have an $IC_{50}$ value for tau deposits of less than 10 nM in a competitive binding assay.

Preferred compounds of the invention, as well as having excellent binding affinity for tau deposits (for example binding for tau at a level described above in a competitive binding assay), are selective tau deposit ligands. "Selective", in this context, means any tau deposit ligand that binds to a tau deposit in preference to an Aβ deposit. For example, preferably compounds of the invention have a binding affinity for tau is at least 1.2 times that for A3, and more preferably at least 1.5 times, more preferably at least 2 times, more preferably at least 3 times, more preferably at least 5 times, more preferably at least 8 times, more preferably at least 10 times, more preferably at least 12 times, and even more preferably at least 15 times, for example at least 18 times, at least 20 times, at least 22 times, at least 25 times, at least 30 times, at least 40 times, at least 50 times, at least 100 times or at least 150 times. In one preferred embodiment, compounds of the invention have a binding affinity for tau that is at least 2 times that for Aβ. In one preferred embodiment, compounds of the invention have a binding affinity for tau that is at least 3 times that for Aβ. In another preferred embodiment, compounds of the invention have a binding affinity for tau that is at least 5 times that for Aβ. In another preferred embodiment, compounds of the invention have a binding affinity for tau that is at least 10 times that for Aβ. In another preferred embodiment, compounds of the invention have a binding affinity for tau that is at least 15 times that for Aβ. In another preferred embodiment, compounds of the invention have a binding affinity for tau that is at least 20 times that for Aβ. In another preferred embodiment, compounds of the invention have a binding affinity for tau that is at least 30 times that for Aβ. In an especially preferred embodiment, compounds of the invention have a binding affinity for tau that is at least 3 times that for Aβ.

In certain very preferred embodiments, compounds of the invention have a binding affinity for tau that is at least 3 times that for Aβ, and have an $IC_{50}$ value for tau deposits of less than 30 nM in a competitive binding assay (and more preferably less than 20 nM, and most preferably less than 10 nM).

It is also preferred that the compounds of the invention have a C Log P that is less than 7.0, preferably less than 6.5, preferably less than 5.0, more preferably less than 4.5, more preferably less than 4.0, more preferably less than 3.5, and more preferably less than 3.0, for example less than 2.8, less than 2.5, less than 2.3, less than 2.0, or less than 1.8.

The compounds of the invention find utility in the diagnosis and/or the treatment or prophylaxis of conditions associated with tau deposits. For example, the compounds of the invention find utility in the diagnosis and/or treatment or prophylaxis of tauopathies, for example: Alzheimer's disease, corticobasal degeneration (CBD), Pick's disease, progressive supranuclear palsy (PSP), Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion-body myositis, chronic traumatic encephalopathy, Down's syndrome, Gerstman-Straussler-Scheinker syndrome, British dementia, familial Danish dementia, dementia pugiiistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.lle383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Straussler-Scheinker with tau, mutations in LRRK2, SLC9A6-related mental retardation, and white matter tauopathy with globular glial inclusions. The compounds of the invention are especially useful in the diagnosis and/or treatment (in particular the diagnosis) of Alzheimer's disease, corticobasal degeneration, Pick's disease, Parkinson's disease, chronic traumatic encephalopathy and progressive supranuclear palsy; and even more especially Alzheimer's disease and corticobasal degeneration.

The compound of the invention may be for use as a therapeutic agent (or medicament) in the treatment of a disease or disorder associated with tau deposits (i.e. tauopathies), such as the tauopathies listed above.

The invention also provides a method for the treatment or prophylaxis of a condition associated with a disease or disorder associated with tau deposits (i.e. tauopathies) in a mammal (in particular in a human), which comprises administering to the mammal a therapeutically effective amount of a compound according to the invention, or a composition comprising a compound according to the invention together with a pharmaceutically acceptable carrier. Clinical conditions mediated by tau deposits that may be treated by the method of the invention are tauopathies, for example the tauopathies listed above.

The invention also provides the use of a compound according to the invention, for the manufacture of a medicament for the treatment or prophylaxis of a condition associated with a disease or disorder associated with tau deposits (i.e. tauopathies), for example the tauopathies listed above.

The compound of the invention may also be used as a diagnostic agents (for in vivo and/or in vitro diagnostic use) for the detection of tau deposits.

The compounds of the invention may be used for diagnostic purposes because they have the ability to target a particular pathology (tau deposits) and can be detected at the desired site. For example, compounds of the invention are able to detect the presence and the level of tau deposits in a patient with or suspected of having a disease or disorder associated with tau deposits (i.e. tauopathies), such as the tauopathies listed above. The compounds of the invention are also especially useful for diagnosis of tauopathies because the compounds of the invention do not show off-target MAO binding or inhibitory activity. As MAO are present in the brain in areas that overlap with tau pathology in certain tauopathies, such off-target effects are undesirable in tau deposit ligands.

The compounds of the invention can bind tau deposits both in vivo and in vitro. The compound of the invention may be for use as a diagnostic agent (for in vivo and/or in vitro diagnostic use) in the diagnosis of disease or disorder associated with tau deposits (i.e. tauopathies), such as the tauopathies listed above.

The compounds of the invention cross the blood-brain barrier to a greater extent than previously disclosed compounds of a similar nature, and also are distributed well across the brain once they have crossed the blood-brain barrier.

When used as a diagnostic agent, the compounds of the invention may optionally be in labeled form, as described above. Thus the present invention also provides the use of a compound of the invention in a labeled form for use as a diagnostic agent for the diagnosis of conditions associated with a disease or disorder associated with tau deposits (i.e. a tauopathy). In such embodiments, preferably the compound of the invention in labeled form comprises one or more radioisotopes selected from $^{3}$H, $^{11}$C, $^{13}$C, $^{14}$C, $^{13}$N, $^{15}$O, $^{18}$F and $^{19}$F, preferably $^{3}$H, $^{11}$C, $^{14}$C, $^{13}$N, $^{15}$O, $^{18}$F and $^{19}$F, more preferably $^{3}$H, $^{11}$C, $^{13}$N, $^{15}$O and $^{18}$F, and most preferably $^{3}$H, and $^{18}$F. When used as a diagnostic agent (especially for in vivo use), and the compound is radioactively labeled, for example with $^{11}$C, $^{13}$N, $^{15}$O or $^{18}$F (preferably $^{18}$F), the compounds of the invention may be detected by positron emission topography. When used as a diagnostic agent (especially for in vitro use), and the compound is radioactively labeled, for example with $^{3}$H, the compounds of the invention may be detected by autoradiography.

As mentioned above, the compounds of the invention may be used for diagnostic purposes because they have the ability to target a particular pathology (tau deposits) and can be detected at the desired site. As such, the compounds of the invention when used as diagnostic agents are especially useful as imaging agents. Imaging agents are compounds that allow the imaging of specific organs, tissues, diseases and physiological functions. Such imaging allows for diagnosing disease, monitoring disease progression, and tracking therapeutic response.

A compound of the invention when used as a diagnostic agent, and in particular as an imaging agent, may be detected via radioscintigraphy, assays, chemilumensence, electrochemiluminescence, near infrared luminescence, fluorescence, spectroscopy, autoradiography, liquid scintillation counting, gamma imaging, magnetic resonance imaging (MRI), magnetic resonance spectroscopy (MRS), scintigraphy, single-photon emission computed tomography (SPECT), computed tomography (CT scan), and/or positron emission tomography (PET).

In embodiments of the invention wherein the compound of the invention is for use as a diagnostic agent, and in particular as an imaging agent, the type of detection instrument available is a major factor in selecting if a label is required, and what label to choose. For example, where imaging requires an isotope to be detected, the type of detection instrument used will guide if a label is needed (i.e. is the isotope naturally occurring or not, and at what abundance is it present in when it occurs naturally), and, if so, what isotope to use. In one aspect, the compound of the invention is labeled, and the form of labeling chosen must have a type of decay detectable by a given type of instrument. Moreover, other considerations such as the half-life of the radioisotopes are taken into account when selecting an isotope label for in vivo imaging.

The compounds of the invention for use as diagnostic agents for in vivo imaging (in particular imaging of tau deposits and/or quantification of tau deposits) are preferably used in conjunction with non-invasive neuroimaging techniques such as in vivo MRS, MRI, PET, SPECT and combinations thereof. A compound of the invention may be labeled with $^{11}$C, $^{13}$N, $^{15}$O or $^{18}$F, for PET imaging. No labeling may be required for in vivo MRS or MRI, or a compound may be labeled with $^{13}$C for MRS or MRI.

The present invention also provides a method of diagnosing a patient or monitoring disease progression in a patient comprising administering a compound of the invention to the patient. The method may further comprise detecting the compound of the invention in vivo at the site of interest in a patient (e.g. the brain) using PET or SPECT, or detecting the compound in a sample from the patient. Preferably in such embodiments the compound of the invention comprises one or more radioisotopes selected from $^{3}$H, $^{11}$C, $^{13}$C, $^{14}$C, $^{13}$N, $^{15}$O, $^{18}$F and $^{19}$F, preferably $^{3}$H, $^{11}$C, $^{14}$C, $^{13}$N, 150, $^{18}$F and $^{19}$F, more preferably $^{3}$H, $^{11}$C, $^{13}$N, $^{15}$O or $^{18}$F, and most preferably $^{3}$H or $^{18}$F. The present invention also provides method of diagnosing a patient or monitoring disease progression in a patient comprising contacting a compound of the invention with a sample taken from the patient.

The method may further comprise detecting the compound of the invention using radioscintigraphy, assays, chemilumensence, electrochemiluminescence, autoradiography, near infrared luminescence, fluorescence, spectroscopy, liquid scintillation counting, gamma imaging, scintigraphy, magnetic resonance imaging (MRI), magnetic resonance spectroscopy (MRS), single-photon emission computed tomography (SPECT), or computed tomography (CT scan).

In the methods of diagnosing a disease or disorder associated with tau deposits as described herein, the method may comprise:

i) administering to the subject a diagnostically effective amount of a compound of the invention;
ii) allowing the compound of the invention to distribute into the tissue of interest (such as brain or body fluids such as cerebrospinal fluid (CSF)); and
iii) imaging the tissue of interest, wherein an increase in binding of the compound of the invention to the tissue of interest compared to a normal or control level of binding indicates that the subject is suffering from or is at risk of developing a disorder associated with tau deposits.

The compounds of the invention can be used for imaging tau deposits in any sample or a specific body part or body area of a patient which suspected to contain tau deposits. The compounds of the invention are particularly suitable for imaging of tau deposits in the brain, as well as in body fluids such as cerebrospinal fluid (CSF).

Diagnosis of a disease or disorder associated with tau deposits in a patient may be achieved by detecting the specific binding of a compound according to the invention to the tau deposits in a sample or in situ, which includes:
(a) bringing the sample or a specific body part or body area suspected to contain the tau deposits (e.g. the brain and/or CSF) into contact with a compound of the invention which binds the tau deposits.
(b) allowing the compound of the invention to bind to the tau deposits to form a compound/tau deposits complex,
(c) detecting the formation of the compound/tau deposits complex,
(d) optionally correlating the presence or absence of the compound/tau deposits complex with the presence or absence of tau deposits in the sample or specific body part or area, and
(e) optionally comparing the amount of the compound/tau deposits complex to a normal or control value, wherein an increase in the amount of the compound/tau deposits complex compared to a normal control value may indicate that the patient is suffering from or is at risk of developing a tau-associated disorder.

After the sample or a specific body part or body area has been brought into contact with the compound of the invention (e.g. the brain and/or CSF), the compound is allowed to bind to the tau deposits. The amount of time required for binding will depend on the type of test (e.g. in vitro or in vivo) and can be determined by a person skilled in the art by routine experiments.

The presence or absence of the compound/tau deposits is then optionally correlated with the presence or absence of tau deposits in the sample or specific body part or area. The amount of the compound/tau deposits complex can be compared to a normal or control value which has been determined in a sample or a specific body part or body area of a healthy subject, wherein an increase in the amount of the compound/tau deposits complex compared to a normal or control value may indicate that the patient is suffering from or is at risk of developing a disease or disorder associated with tau deposits (i.e. a tauopathy).

The present invention also relates to a method of determining the amount of tau deposits in a tissue and/or a body fluid. This method comprises the steps of:
(1) providing a sample representative of the tissue and/or body fluid under Investigation (e.g. the brain and/or CSF);
(2) testing the sample for the presence of tau deposits with a compound of the invention;
(3) determining the amount of compound bound to the tau deposits; and
(4) calculating the amount of tau deposits in the tissue and/or body fluid.

The sample can be tested for the presence of tau deposits with a compound of the invention by bringing the sample into contact with a compound of the invention, allowing the compound of the invention to bind to the tau deposits to form a compound/tau deposit complex and detecting the formation of the compound/tau deposit as explained above.

Monitoring minimal residual disorder in a patient suffering from a disorder associated with tau deposits who has been treated with a therapeutic agent useful in the prevention or treatment of a disorder associated with tau deposits (for example a therapeutic agent useful in the prevention or treatment of one or more or the tauopathies listed above) may be achieved by:
carrying out steps (a) to (d) above; and (e) optionally comparing the amount of the compound/tau deposit complex to a normal or control value, wherein an increase in the amount of the complex compared to a normal or control value may indicate that the patient may still suffer from a minimal residual disease.

How steps (a) to (e) can be conducted has already been explained above.

Predicting responsiveness of a patient suffering from a disorder associated with tau deposits and being treated with a therapeutic agent useful in the prevention or treatment of a disorder associated with tau deposits can be achieved by
carrying out steps (a) to (d) above; and (e) optionally comparing the amount of the compound/tau deposit complex to a normal or control value.

How steps (a) to (e) can be conducted has already been explained above.

In the method for predicting responsiveness the amount of the compound/tau deposits complex can be optionally compared at various points of time during the treatment, for instance, before and after onset of the treatment or at various points of time after the onset of the treatment. A change, especially a decrease, in the amount of the compound/tau deposits complex may indicate that the patient has a high potential of being responsive to the respective treatment.

A compound according to the invention can also be incorporated into a test kit for detecting tau deposits. The test kit typically comprises a container holding one or more compounds according to the Invention and instructions for using the compound for the purpose of binding to tau deposits to form a compound/tau deposit complex and detecting the formation of the compound/tau deposit complex such that presence or absence of the compound/tau deposit complex correlates with the presence or absence of the tau deposits.

Dosing

The amount of compound of the invention which is required to achieve a diagnostic or therapeutic effect will, of course, vary with the particular compound, the route of administration, the subject under treatment, including the type, species, age, weight, sex, and medical condition of the subject and the renal and hepatic function of the subject, and the particular disorder or disease being treated, diagnosed or monitored, as well as its severity. An ordinarily skilled physician, veterinarian or clinician can readily determine and prescribe the effective amount of the drug required to prevent, counter or arrest the progress of the condition or be used to diagnose a condition or the progression of a condition.

Oral dosages of the present invention, when used as a diagnostic or therapeutic agent, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the compound of the invention for the symptomatic adjustment of the dosage to the patient to be treated. A medicament typically contains from about 0.01 mg to about 500 mg of the compound of the invention, preferably from about 1 mg to about 100 mg of compound of the invention. Intravenously, the most preferred doses will range from about 0.1 to about 10 mg/kg/minute during a constant rate infusion. Advantageously, compounds of the invention may be administered in a single daily dose, or the total daily dosage may be administered in divided doses of two, three or four times daily. For diagnostic use, preferably the compounds of the invention may be administered in a single daily dose. Furthermore, preferred compounds for the invention can be administered in intranasal form via topical use of suitable intranasal vehicles, or via transdermal routes, using those forms of transdermal skin patches well known to those of ordinary skill in the art.

While it is possible for a compound of the invention to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier. Pharmaceutical compositions of the invention may take the form of a pharmaceutical formulation as described below.

Formulations

"Pharmaceutical" as used here does not necessarily mean therapeutic, for example, a pharmaceutical formulation may be used as a diagnostic agent, such as an imaging agent. The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient to be treated or diagnosed.

The formulations may conveniently be presented in unit dosage form and may be prepared by any of the methods well known in the art of pharmacy. All methods include the step of bringing the compound of the invention into association with the carrier which constitutes one or more accessory ingredients. In general the formulations are prepared by uniformly and intimately bringing into association the compound of the invention with liquid carriers or finely divided solid carriers or both and then, if necessary, shaping the product into the desired formulation.

Formulations of the invention suitable for oral administration may be presented as discrete units such as capsules, cachets, pills or tablets each containing a predetermined amount of the compound of the invention; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The compound of the invention may also be presented as a bolus, electuary or paste.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for topical administration in the mouth, for example buccally or sublingually, include lozenges comprising the compound of the invention in a flavoured basis such as sucrose and acacia or tragacanth, and pastilles comprising the compound of the invention in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the compound of the invention.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient (i.e. sole therapeutic agent or sole diagnostic agent) in a medicament, it is also possible for the compound to be used in combination with one or more further active ingredient. For example, a compound of the invention may be used as the sole diagnostic agent in a diagnostic composition, or it is also possible for the compound to be used in combination with one or more further diagnostic agents and/or one or more therapeutic agents. Alternatively, a compound of the invention may be used as the sole diagnostic agents and/or therapeutic agent in a medicament, or it is also possible for the compound to be used in combination with one or more further therapeutic agents and/or one or more diagnostic agents.

Thus, the invention also provides a compound according to the invention together with a further diagnostic agent, for simultaneous, sequential or separate administration. Such further diagnostic agents may be further compounds according to the invention, or they may be different diagnostic agents. The further diagnostic agent may be an agent useful in the diagnosis of tauopathies (for example the tauopathies listed above).

In certain preferred embodiments, the further diagnostic agent may be an agent that is selective for Aβ deposits useful in diagnosis of Alzheimer's disease. The further diagnostic agent may be detectable by radioscintigraphy, magnetic resonance imaging (MRI), assays, chemilumensence, near infrared luminescence, fluorescence, autoradiography, liquid scintillation counting, gamma imaging, scintigraphy, magnetic resonance imaging, magnetic resonance spectroscopy, SPECT, computed tomography (CT scan) and/or positron emission tomography (PET). Preferably, the further diagnostic agent is detectable by positron emission tomography. For example, the further agent may be a PET ligand.

For example, the compounds of the invention may be effectively administered in combination with (or may be used in vitro for in vitro diagnosis with) effective amounts of one or more other diagnostic agents, for example one or more diagnostic agents selected from the group consisting of luminescent conjugated oligothiophenes (e.g. q-FTAA-CN, p-FTAA-CN, h-FTAA-CN), Pittsburgh compound B (PiB), fludeoxyglucose F 18 (FDG), florbetapir, flutemetamol, NAV4694, PBB3, AT-100, 4G8, Congo red, Thioflavin S, Thioflavin T, m-I-stilbene, chrysamine G, BF-277, TZDM, FDDNP, MeO-X-04, IMPY, NIAD-4 $^{3}$H—X-34, luminescent conjugated polythiophenes (e.g. polythiophene acetic acid (PTAA), tPTAA, POWT, tPOWT, POMT, tPOMY) and GTP1 (Genentech Tau Probe 1).

The invention further provides a compound according to the invention together with a further therapeutic agent, for simultaneous, sequential or separate administration. Such further therapeutic agents may be further compounds according to the invention, or they may be different therapeutic agents, for example an agent useful in the prevention or treatment of one or more or the tauopathies listed above. For example, the compounds of the invention may be effectively administered in combination with effective amounts of other agents, for example one or more agents selected from the group consisting antibodies (for example active immunisation (e.g. ACI-35 (AC Immune/Janssen), and AADvac1 (Axon Neuroscience)), passive immunization (e.g. tau antibodies, such as BMS-986168 (IPN007, Bristol-Myers Squibb Company), C2N-8E12 (C2N/AbbVie), and RG6100 (RO7105705, AC Immune/Genentech; aducanumab; solanezumab; gantenerumab; and crenezumab), RG7345 (RO6926496, MAb86, F. Hoffmann-La Roche), PHF1, 4E6G7, 6B2G12), MK-8719 (Merck & Co.), TPI-287 (Cortice Biosciences), methylene blue (for example TRx 0327 and Rember), dopaminergic treatments (for example levodopa, caridopa, dopamine agonists (e.g. bromocriptine, perfolide, pramipexole, ropinirole)), cholinesterase inhibitors (e.g. tacrine, donepezil, rivastigmine, galantamine), monoamine oxidase inhibitors (e.g. selegiline), antocholinerginc agents (e.g. trihexyphenidyl, benztropine mesylate, biperiden, procyclidine), antihistamines (e.g. diphenhydramine), antipsychotic drugs, analgesic drugs, anti-inflammatories, riluzole, non-steroidal anti-inflammatory drugs, caffein A2A receptor antagonists, CERE-120 (adeno-associated virus serotype 2-neurturin), amantadine, tolcapone, entacapone, ethosuximide, trazodone, and dibenzoylmethane.

The above other diagnostic and therapeutic agents, when employed in combination with the compounds of the invention, may be used, for example, in those amounts indicated in the Physicians' Desk Reference (PDR) or as otherwise determined by one of ordinary skill in the art.

The compounds of the invention as described above, optionally in labeled form, also find use as a reference compound in methods of identifying ligands for the tau deposits. Thus, the invention provides a method of identifying a ligand for tau deposits which comprises use of a compound of the invention or a compound of the invention in labeled form, as a reference compound. For example, such a method may involve a competitive binding experiment in which binding of a compound of the invention to the tau deposits is reduced by the presence of a further compound which has tau deposits-binding characteristics, for example stronger tau deposits-binding characteristics than the compound of the invention in question.

EXPERIMENTAL

General Information

All reagents and solvents used were analytical grade and commercially available. Anhydrous reactions were routinely used for reactions. Reactions were typically run under inert atmosphere of nitrogen ($N_2$).

$^{1}$H and $^{13}$C Spectra were recorded on a Bruker 500 NMR spectrometer.

Mass spectra were recorded on a Waters Acquity QDa LSMS. The mass spectrometer was equipped with an electrospray ion source (ES) operating in a positive or negative mode. The capillary voltage was 3.5 kV and the cone voltage was 30 V. The mass spectrometer was scanned between m/z 100-850 with a scan time of 0.5 s. The column temperature was set to 50° C. with a linear gradient starting at 95% A (A: 10 mM $NH_4HCO_3$) and ending in 100% B (B:MeCN). The column used was an Acquity UPLC™ HSS $C_{18}$ 1.7 μm, 2.1×50 mm run at 0.4 ml/min.

The HPLC used was an Agilent 1100 coupled to an Agilent 1290 Infinity DAD. The column used was an XBridge $C_{18}$ 3.5 μm, 3.0×50 mm run at 0.8 ml/min. The column temperature was set to 50° C. with a linear gradient starting at 98-2% A over 3.5 min (A: 10 mM $NH_4HCO_3$) then holding 98% B (B:MeCN) for 1.5 min.

The semi-prep HPLC was a Gilson with a 322 pump. The column used was a Kromasil $C_8$ 7 μm, 20×250 mm.

Microwave heating was performed in a Biotage Initiator 2.0.

Chromatography separations were performed using silica gel 60 (0.040-0.063 mm) in a filter funnel or by using a Teledyne ISCO CombiFlash Rf with varying sizes (4-120 g) of Silicycle silica columns. TLC plates were Merck silica gel 60 $F_{254}$.

The term room temperature (rt) means, unless otherwise specified, a temperature between 16 and 25° C. The term reflux means, unless otherwise stated, in reference to an employed solvent using a temperature at or slightly above the boiling point of the named solvent.

Example Compound 1: 2-{2-Fluoro-6-[(3S)-3-methoxypiperidin-1-yl]pyridin-3-yl}-1H-indol-5-ol

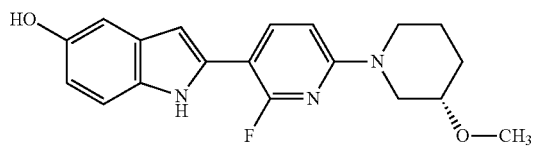

Method 1

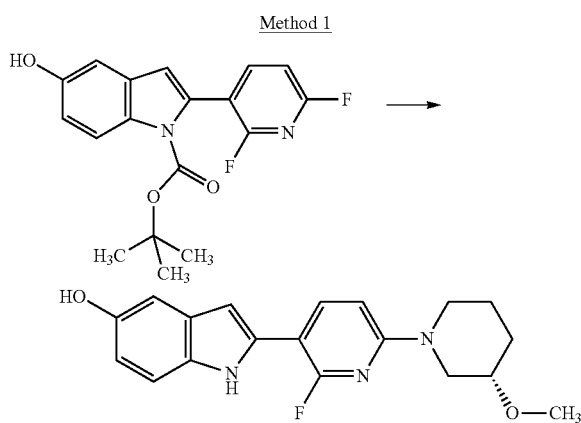

In a 20 ml microwave vial were t-butyl 2-(2,6-difluoro-pyridin-3-yl)-5-hydroxy-1H-indole-1-carboxylate (125 mg, 0.36 mmol, see WO2021074351 A1 for method of manufacture) and 3-(S)-methoxypiperidine HCl (62 mg, 1.1 eq) suspended in acetonitrile (4 ml). To the solution Hunig's base (160 μl, 2.5 eq) was added and the reaction was subjected to the microwave for 60 min at 150° C.

The solvent was removed in vacuo, the remains were taken into ethyl acetate, washed with water, treated with brine, dried over MgSO$_4$, and then filtered. The solvent was removed in vacuo to give the crude.

The crude was purified on the ISCO (12 g silica, applied with dichloromethane (DCM), eluted with 20-40% ethyl acetate/hexane over 8 min). DCM was added to the remains, the solid was then filtered and washed with DCM to give 2-{2-fluoro-6-[(3S)-3-methoxypiperidin-1-yl]pyridin-3-yl}-1H-indol-5-ol (31 mg solid, 25% yield, HPLC Rf 2.92 min, MS m/z (M+1) 342.2, (M-1) 340.2, TLC: 40% ethyl acetate/hexane Rf 0.15), $^1$H NMR (400 MHz, DMSO) δ 11.00 (s, 1H), 8.69 (s, 1H), 8.12 (dd, J=10.7, 8.6 Hz, 1H), 7.23 (dt, J=8.6, 0.7 Hz, 1H), 6.91 (dd, J=8.6, 2.1 Hz, 1H), 6.87 (d, J=2.3 Hz, 1H), 6.65 (dd, J=8.6, 2.3 Hz, 1H), 6.60-6.53 (m, 1H), 3.97 (d, J=12.1 Hz, 1H), 3.75 (ddd, J=13.0, 6.3, 3.7 Hz, 1H), 3.36 (s, 7H), 2.08-1.91 (m, 1H), 1.79 (ddt, J=13.4, 6.8, 3.4 Hz, 1H), 1.67-1.42 (m, 2H).

$^{13}$C NMR (101 MHz, DMSO) δ 178.10, 150.80, 139.09, 131.69, 131.62, 131.02, 129.33, 111.50, 111.33, 103.81, 103.49, 99.29, 99.22, 74.19, 55.54, 47.97, 44.65, 40.12, 39.91, 39.70, 39.49, 39.28, 39.07, 38.87, 29.39, 21.60.

$^{19}$F NMR (377 MHz, DMSO) δ −67.79, −67.82.

Method 2

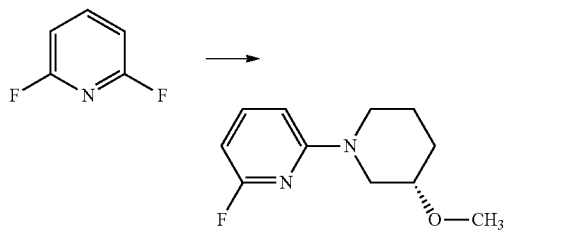

Step (i) 2-Fluoro-6-[(3S)-3-methoxypiperidin-1-yl]pyridine (S)-3-Methoxypiperidine HCl (1.0 g, 6.6 mmol) was slurried in dioxane (8 ml) and 2,6-difluoropyridine (660 μl, 1.1 eq) was added, followed by Hunig's base (3.0 ml, 2.6 eq). The reaction was heated to 100° C. for 5 h.

The cooled reaction mixture was taken into ethyl acetate, washed with water, treated with brine, dried over MgSO$_4$, and then filtered. The solvent was removed in vacuo to give the crude oil.

The crude oil was purified on the ISCO (40 g silica, applied with hexane, eluted with 5-20% ethyl acetate/hexane over 5 min) to give 2-fluoro-6-[(3S)-3-methoxypiperidin-1-yl]pyridine (1.03 g oil, HPLC Rf 2.90 min, 75% yield, MS m/z (M+1) 211.2 (very weak), TLC 10% ethyl acetate/hexane Rf 0.14).

$^1$H NMR (500 MHz, DMSO-d6) δ 7.59 (ddd, J=9.2, 8.3, 7.7 Hz, 1H), 6.69-6.60 (m, 1H), 6.16 (ddd, J=7.7, 2.9, 0.4 Hz, 1H), 3.86 (dq, J=11.0, 1.3 Hz, 1H), 3.64 (ddd, J=13.2, 5.6, 3.9, 0.9 Hz, 1H), 3.25 (s, 3H), 3.24-3.15 (m, 3H), 1.95-1.84 (m, 1H), 1.68 (dddd, J=13.3, 7.2, 6.0, 3.5 Hz, 1H), 1.52-1.43 (m, 1H), 1.39 (dtt, J=13.2, 9.2, 3.7 Hz, 1H).

$^{13}$C NMR (126 MHz, DMSO-d6) δ 163.41, 161.56, 158.28, 158.15, 142.90, 142.83, 103.56, 103.52, 94.90, 94.61, 74.64, 55.93, 48.37, 45.00, 29.95, 22.09.

Step (ii) 3-Bromo-2-fluoro-6-[(3S)-3-methoxypiperidin-1-yl]pyridine

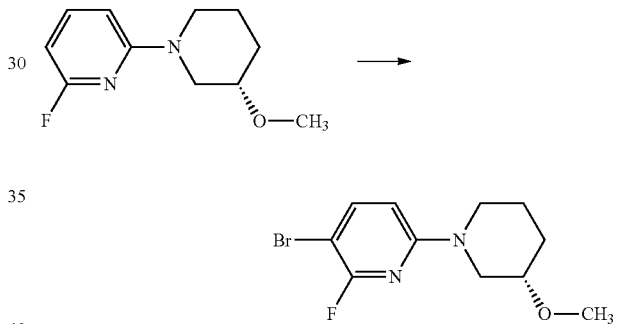

2-Fluoro-6-[(3S)-3-methoxypiperidin-1-yl]pyridine (1.03 g, 4.9 mmol) was dissolved in acetonitrile (20 ml), cooled on an ice-bath and NBS (0.87 g, 1 eq) was added in 2 portions. The reaction was allowed to stir at 0° C. for 5 min then stirred at rt for 30 min.

Ether was added to the mixture, the solution was washed with water, treated with brine, dried over MgSO$_4$, and then filtered. The solvent was removed in vacuo stripped to give the crude.

The crude was purified on the ISCO (40 g silica, applied with hexane/DCM, eluted with 5-20% ethyl acetate/hexane over 5 min) to give 3-bromo-2-fluoro-6-[(3S)-3-methoxypiperidin-1-yl]pyridine (1.35 g oil, HPLC Rf 3.31 min, 96% yield, MS m/z (M+1) 289.0, 291.0, TLC 20% ethyl acetate/hexane Rf 0.19).

$^1$H NMR (500 MHz, DMSO-d6) δ 7.75 (dd, J=9.6, 8.7 Hz, 1H), 6.67 (dd, J=8.8, 1.9 Hz, 1H), 3.78 (ddt, J=12.9, 3.2, 1.1 Hz, 1H), 3.57 (ddd, J=13.3, 6.7, 3.8 Hz, 1H), 3.33-3.25 (m, 2H), 3.24-3.19 (m, 1H), 1.87 (dqd, J=11.3, 3.8, 1.9 Hz, 1H), 1.72-1.61 (m, 1H), 1.54-1.46 (m, 1H), 1.43-1.34 (m, 1H).

$^{13}$C NMR (126 MHz, DMSO-d6) δ 158.61, 157.07, 156.95, 156.78, 144.96, 144.94, 106.04, 106.01, 85.85, 85.54, 74.51, 55.98, 48.40, 45.16, 29.70, 21.85.

Step (iii) t-Butyl 5-[(t-butyldimethylsilyl)oxy]-2-{2-fluoro-6-[(3S)-3-methoxypiperidin-1-yl]pyridin-3-yl}-1H-indole-1-carboxylate

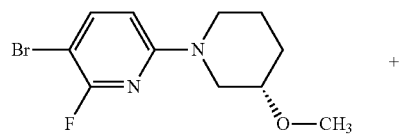

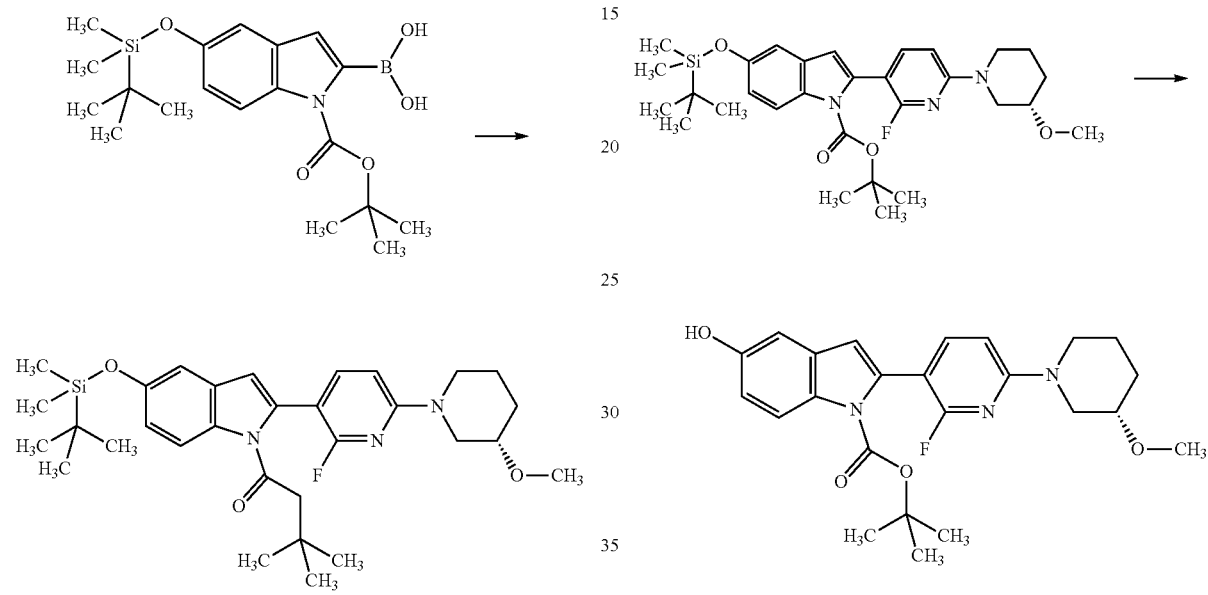

3-Bromo-2-fluoro-6-[(3S)-3-methoxypiperidin-1-yl]pyridine (580 mg, 2 mmol) and {1-[(t-butoxy)carbonyl]-5-[(t-butyldimethylsilyl)oxy]-1H-indol-2-yl}boronic acid (1.1 g, 1.4 eq) were dissolved in dioxane (12 ml) in a 20 ml microwave vial. The solution was bubbled with N₂ for 5 min, then [1,1'-Bis(diphenylphosphino)ferrocene]dichloropalladium(II), complexed with dichloromethane (Pd(dppf)Cl₂ DCM; 82 mg, 5 mol %) was added followed by 2 M K₂CO₃ (3 ml, 3 eq). The solution was again bubbled with N₂ for 5 min, capped then put in a pre-heated oil bath. The reaction was heated to 90° C. for 1 h.

The aqueous fraction was removed from the cooled reaction, and the organic fraction was diluted with ethyl acetate, dried over MgSO₄, and then filtered. The solvent was removed in vacuo to give the crude.

The crude was purified on the ISCO (40 g silica, applied with DCM, eluted with 5-15% ethyl acetate/hexane over 6 min) to give t-butyl 5-[(t-butyldimethylsilyl)oxy]-2-{2-fluoro-6-[(3S)-3-methoxypiperidin-1-yl]pyridin-3-yl}-1H-indole-1-carboxylate (1.17 g foam, 98% yield, HPLC Rf 4.43 min, MS m/z (M+1) 556.7, TLC 20% ethyl acetate/hexane Rf 0.35).

¹H NMR (500 MHz, DMSO-d6) δ 7.92 (dt, J=8.9, 0.7 Hz, 1H), 7.66 (dd, J=10.2, 8.3 Hz, 1H), 7.01 (dd, J=2.4, 0.5 Hz, 1H), 6.83 (dd, J=8.9, 2.5 Hz, 1H), 6.76 (dd, J=8.4, 2.1 Hz, 1H), 6.59 (d, J=0.7 Hz, 1H), 3.89 (dd, J=13.1, 3.3 Hz, 1H), 3.67 (ddd, J=13.2, 6.4, 3.8 Hz, 1H), 3.62-3.52 (m, 4H), 3.39-3.31 (m, 2H), 3.27 (s, 3H), 3.24 (tt, J=7.4, 3.4 Hz, 1H), 1.92 (ddt, J=11.4, 7.4, 3.8 Hz, 1H), 1.78-1.65 (m, 5H), 1.53 (dtd, J=12.5, 8.3, 3.9 Hz, 1H), 1.45-1.36 (m, 1H), 1.34 (s, 9H), 0.95 (s, 9H).

¹³C NMR (126 MHz, DMSO-d6) δ 150.88, 149.35, 142.06, 133.99, 131.56, 129.63, 117.46, 115.44, 110.20, 109.68, 102.72, 102.44, 102.19, 83.27, 74.16, 67.01, 55.57, 48.08, 44.84, 29.53, 27.18, 25.63, 25.12, 21.57, 17.98, −4.53.

Step (iv) t-Butyl 2-{2-fluoro-6-[(3S)-3-methoxypiperidin-1-yl]pyridin-3-yl}-5-hydroxy-1H-indole-1-carboxylate t-Butyl 5-[(t-butyldimethylsilyl)oxy]-2-{2-fluoro-6-[(3S)-3-methoxypiperidin-1-yl]pyridin-3-yl}-1H-indole-1-carboxylate (1.1 g, 2.0 mmol) was dissolved in tetrahydrofuran (THF; 20 ml), cooled on an ice-bath and a 1 M tetrabutylammonium fluoride (TBAF) solution (2.2 ml, 1.1 eq) was added. The reaction was stirred for 10 min at 0° C.

The reaction was diluted with ethyl acetate, treated with brine, dried over MgSO₄, and then filtered. The solvent was removed in vacuo to give the crude.

The crude was purified on the ISCO (40 g silica, applied with DCM, eluted with 30-45% ethyl acetate/hexane over 5 min) to give t-butyl 2-{2-fluoro-6-[(3S)-3-methoxypiperidin-1-yl]pyridin-3-yl}-5-hydroxy-1H-indole-1-carboxylate (0.84 g foam, HPLC 3.41 min, MS m/z (M+1) 442.2, (M-1) 440.2, 98% yield, TLC Rf 45% ethyl acetate/hexane Rf 0.28).

¹H NMR (500 MHz, DMSO-d6) δ 9.18 (s, 1H), 7.87 (dt, J=8.8, 0.7 Hz, 1H), 7.63 (dd, J=10.2, 8.3 Hz, 1H), 6.89 (dd, J=2.5, 0.5 Hz, 1H), 6.77 (dd, J=8.9, 2.5 Hz, 1H), 6.72 (dd, J=8.4, 2.1 Hz, 1H), 6.53 (d, J=0.7 Hz, 1H), 3.88 (dd, J=13.1, 3.3 Hz, 1H), 3.65 (ddd, J=13.2, 6.3, 3.8 Hz, 1H), 3.36-3.28 (m, 3H), 3.22 (tt, J=7.4, 3.4 Hz, 1H), 1.94-1.85 (m, 1H), 1.69 (dtt, J=13.4, 6.9, 3.5 Hz, 1H), 1.52 (tdd, J=12.5, 7.7, 3.9 Hz, 1H), 1.45-1.35 (m, 1H), 1.33 (s, 8H).

¹³C NMR (126 MHz, DMSO-d6) δ 170.31, 159.27, 157.41, 157.17, 157.04, 153.33, 149.45, 142.00, 141.97, 133.62, 133.58, 130.25, 129.71, 115.39, 113.35, 109.69, 104.99, 102.73, 102.67, 102.64, 102.49, 83.11, 82.96, 74.17, 59.75, 55.56, 48.11, 44.85, 30.96, 29.53, 27.20, 22.07, 21.57, 20.74, 20.04, 14.07, 13.95, 13.92.

Step (v) 2-{2-Fluoro-6-[(3S)-3-methoxypiperidin-1-yl]pyridin-3-yl}-1H-indol-5-ol

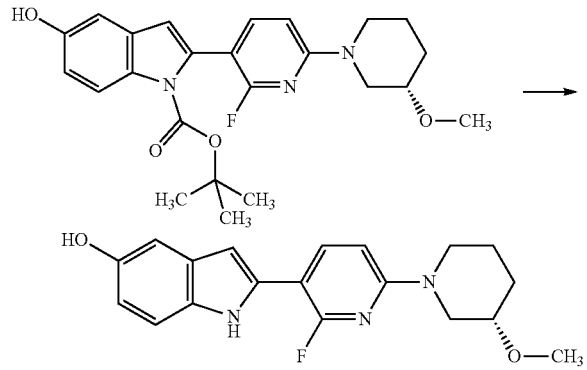

In a 20 ml microwave vial, t-butyl 2-{2-fluoro-6-[(3S)-3-methoxypiperidin-1-yl]pyridin-3-yl}-5-hydroxy-1H-indole-1-carboxylate (0.84 g, 1.9 mml) was dissolved in methanol (15 ml). The reaction was subjected to the microwave for 45 min at 150° C.

The solvent was removed, the remains were stirred with DCM, and the solid was filtered to give 2-{2-fluoro-6-[(3S)-3-methoxypiperidin-1-yl]pyridin-3-yl}-1H-indol-5-ol (300 mg solid, HPLC 2.92 min, MS m/z (M+1) 342.2, (M-1) 340.2, 47% yield, TLC Rf 40% ethyl acetate/hexane Rf 0.15).

See Example Compound 1, Method 1 for spectral data.

Example Compound 2: 2-{2-Fluoro-6-[(3R)-3-methoxypiperidin-1-yl]pyridin-3-yl}-1H-indol-5-ol

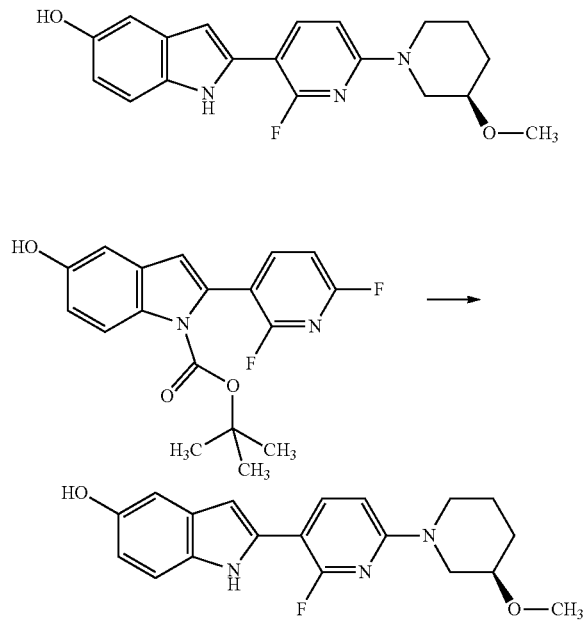

In a 20 ml microwave vial, t-butyl 2-(2,6-difluoropyridin-3-yl)-5-hydroxy-1H-indole-1-carboxylate (125 mg, 0.36 mmol, see WO2021074351 A1 for method of manufacture) and 3-(R)-methoxypiperidine HCl (62 mg, 1.1 eq) were suspended in acetonitrile (4 ml). To the solution Hunig's base (160 μl, 2.5 eq) was added and the reaction was subjected to the microwave for 60 min at 150° C.

The solvent was removed in vacuo, the remains were taken into ethyl acetate, washed with water, treated with brine, dried over MgSO₄, and then filtered. The solvent was removed in vacuo to give the crude.

The crude was purified on the ISCO (12 g silica, applied with DCM, eluted with 20-40% ethyl acetate/hexane over 8 min. DCM was added to the remains, the solid was filtered, and then washed with DCM to give 2-{2-fluoro-6-[(3S)-3-methoxypiperidin-1-yl]pyridin-3-yl}-1H-indol-5-ol (24 mg solid, 25% yield, HPLC Rf 2.92 min, MS m/z (M+1) 342.2, (M-1) 340.2, TLC: 40% ethyl acetate/hexane Rf 0.15).

Example Compound 3: 2-{2-Fluoro-6-[(3S)-3-methoxypiperidin-1-yl]pyridin-3-yl}-1H-indol-6-ol

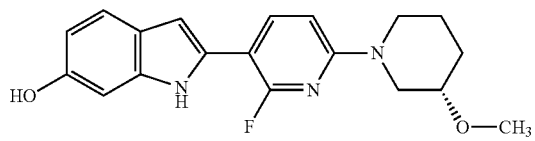 [SMILES: CO[C@H]1CCCN(c2ccc(-c3cc4ccc(O)cc4[nH]3)c(F)n2)C1]

Step (i) t-Butyl 6-[(t-butyldimethylsilyl)oxy]-2-{2-fluoro-6-[(3S)-3-methoxypiperidin-1-yl]pyridin-3-yl}-1H-indole-1-carboxylate

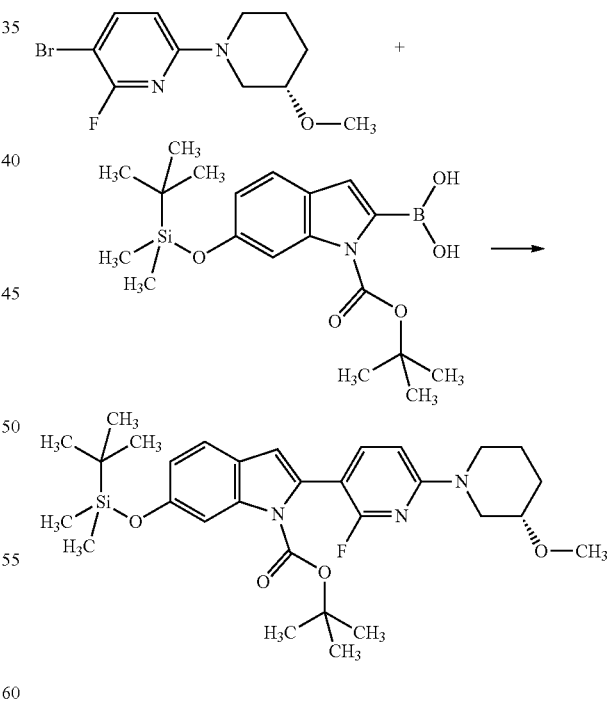

3-Bromo-2-fluoro-6-[(3S)-3-methoxypiperidin-1-yl]pyridine (263 mg, 0.91 mmol, see Example Compound 1, Method 2, Step (ii) for method of manufacture) and {1-[(t-butoxy)carbonyl]-6-[(t-butyldimethylsilyl)oxy]-1H-indol-2-yl}boronic acid (500 mg, 1.4 eq) were dissolved in dioxane (6 ml) in a 20 ml microwave vial. The solution was bubbled with N₂ for 5 min, then Pd(dppf)Cl₂ DCM (40 mg, 5 mol %)

was added, followed by 2 M K₂CO₃ (1.4 ml, 3 eq). The solution was again bubbled with N₂ for 5 min. The reaction was capped then put in a pre-heated oil bath. The reaction was heated to 90° C. for 1 h.

The aqueous fraction was removed from the cooled reaction, and the organic fraction was diluted with ethyl acetate, dried over MgSO₄, and then filtered. The solvent was removed in vacuo to give the crude.

The crude was purified on the ISCO (40 g silica, applied with DCM, eluted with 10-20% ethyl acetate/hexane over 6 min) to give t-butyl 6-[(t-butyldimethylsilyl)oxy]-2-{2-fluoro-6-[(3S)-3-methoxypiperidin-1-yl]pyridin-3-yl}-1H-indole-1-carboxylate (329 mg foam, yield 66%, HPLC Rf 4.77 min, MS m/z (M+1) 556.3, TLC 20% ethyl acetate/hexane Rf 0.25).

Step (ii) t-Butyl 2-{2-fluoro-6-[(3S)-3-methoxypiperidin-1-yl]pyridin-3-yl}-6-hydroxy-1H-indole-1-carboxylate

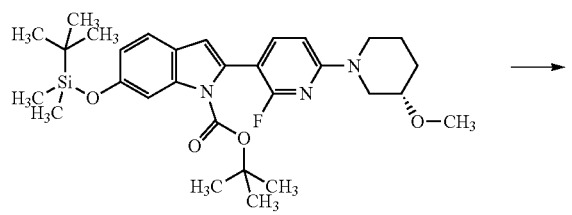

t-Butyl 6-[(t-butyldimethylsilyl)oxy]-2-{2-fluoro-6-[(3S)-3-methoxypiperidin-1-yl]pyridin-3-yl}-1H-indole-1-carboxylate (329 mg, 0.59 mmol) was dissolved in THF (10 ml), cooled on an ice-bath and a 1 M TBAF solution (650 µl, 1.1 eq) was added. The reaction was stirred for 10 min at 0° C.

The reaction was diluted with ethyl acetate, treated with brine, dried over MgSO₄, and then filtered. The solvent was removed in vacuo to give the crude.

The crude was purified on the ISCO (12 g silica, applied with DCM, eluted with 20-35% ethyl acetate/hexane over 4 min) to give t-butyl 2-{2-fluoro-6-[(3S)-3-methoxypiperidin-1-yl]pyridin-3-yl}-6-hydroxy-1H-indole-1-carboxylate (242 mg film, HPLC 3.54 min, MS m/z (M+1) 442.2, (M-1) 440.2, 93% yield, TLC Rf 30% ethyl acetate/hexane Rf 0.16).

Step (iii) 2-{2-Fluoro-6-[(3S)-3-methoxypiperidin-1-yl]pyridin-3-yl}-1H-indol-6-ol

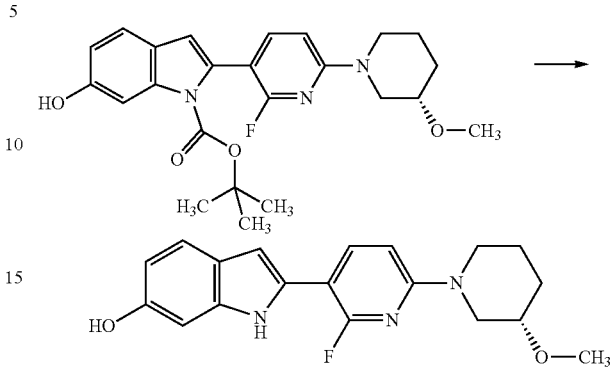

In a 5 ml microwave vial, t-butyl 2-{2-fluoro-6-[(3S)-3-methoxypiperidin-1-yl]pyridin-3-yl}-6-hydroxy-1H-indole-1-carboxylate (0.24 g, 0.54 mml) was dissolved in methanol (4 ml). The reaction was subjected to the microwave for 60 min at 150° C.

The solvent was removed in vacuo, and the crude was purified on the ISCO (12 g silica, applied with DCM (poor solubility), eluted with 40-50% ethyl acetate/hexane over 3 min). to give 2-{2-fluoro-6-[(3S)-3-methoxypiperidin-1-yl]pyridin-3-yl}-1H-indol-6-ol (133 mg solid, HPLC 3.01 min, MS m/z (M+1) 342.2, (M-1) 340.1, 72% yield, TLC Rf 30% ethyl acetate/hexane Rf 0.16).

Example Compound 4: 2-{2-Fluoro-6-[(3R)-3-methoxypiperidin-1-yl]pyridin-3-yl}-1H-indol-6-ol

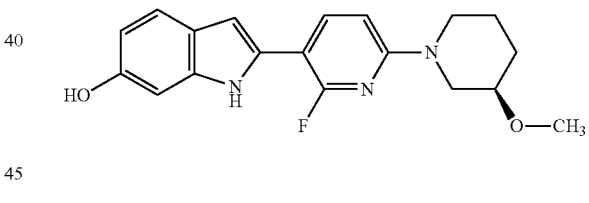

Step (i) 2-Fluoro-6-[(3R)-3-methoxypiperidin-1-yl]pyridine

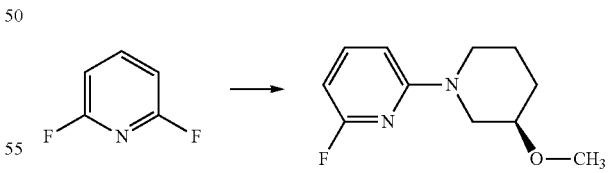

(R)-3-Methoxypiperidine HCl (0.73 g, 4.8 mmol) was slurried in dioxane (4 ml) and 2,6-difluoropyridine (530 µl, 1.2 eq) was added followed by Hunig's base (2.2 ml, 2.6 eq). The reaction was heated to 100° C. overnight.

The cooled reaction mixture was taken into ethyl acetate, washed with water, treated with brine, dried over MgSO₄, and then filtered. The solvent was removed in vacuo to give the crude oil.

The crude oil was purified on the ISCO (40 g silica, applied with hexane, eluted with 5-20% ethyl acetate/hexane over 5 min) to give 2-fluoro-6-[(3R)-3-methoxypiperidin-1-yl]pyridine (0.85 g oil, HPLC Rf 2.90 min, 85% yield, MS m/z (M+1) 211.2 (very weak), TLC 10% ethyl acetate/hexane Rf 0.14).

Step (ii) 3-Bromo-2-fluoro-6-[(3R)-3-methoxypiperidin-1-yl]pyridine

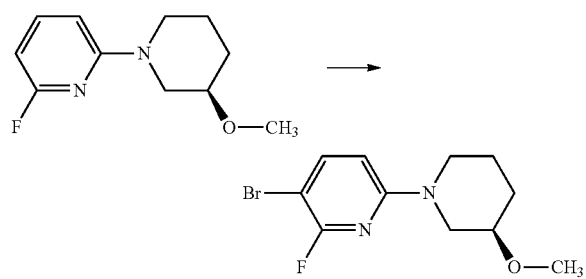

2-Fluoro-6-[(3R)-3-methoxypiperidin-1-yl]pyridine (0.85 g, 4.0 mmol) was dissolved in acetonitrile (15 ml), cooled on an ice-bath and N-bromosuccinimide (NBS; 0.72 g, 1 eq) was added in 2 portions. The reaction was allowed to stir at 0° C. for 5 min then stirred at rt for 30 min.

Diethyl ether was added to the mixture, the solution was washed with water, treated with brine, dried over $MgSO_4$, and then filtered. The solvent was removed in vacuo to give the crude.

The crude was purified on the ISCO (40 g silica, applied with hexane/DCM, eluted with 5-20% ethyl acetate/hexane over 5 min) to give 3-bromo-2-fluoro-6-[(3R)-3-methoxypiperidin-1-yl]pyridine (1.13 g oil, HPLC Rf 3.31 min, 97% yield, MS m/z (M+1) 289.0, 291.0, TLC 20% ethyl acetate/hexane Rf 0.19).

Step (iii) t-Butyl 6-[(t-butyldimethylsilyl)oxy]-2-{2-fluoro-6-[(3R)-3-methoxypiperidin-1-yl]pyridin-3-yl}-1H-indole-1-carboxylate

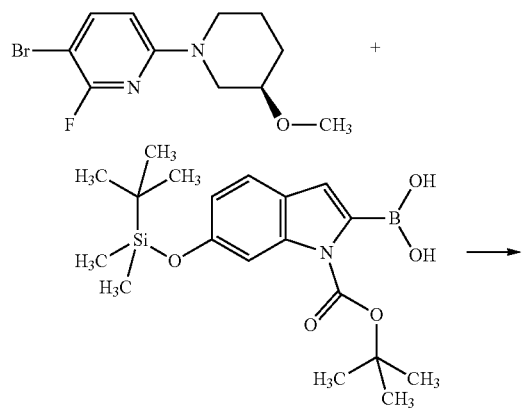

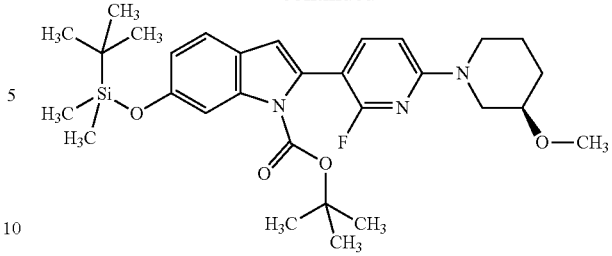

3-Bromo-2-fluoro-6-[(3R)-3-methoxypiperidin-1-yl]pyridine (145 mg, 0.5 mmol) and {1-[(t-butoxy)carbonyl]-6-[(t-butyldimethylsilyl)oxy]-1H-indol-2-yl}boronic acid (300 mg, 1.5 eq) were dissolved in dioxane (3 ml) in a 20 ml microwave vial. The solution was bubbled with $N_2$ for 5 min, then Pd(dppf)Cl$_2$ DCM (20 mg, 5 mol %) was added followed by 2 M $K_2CO_3$ (0.75 ml, 3 eq). The solution was again bubbled with $N_2$ for 5 min. The reaction was capped then put in a pre-heated oil bath. The reaction was heated to 90° C. for 1 h.

The aqueous fraction was removed from the cooled reaction, and the organic fraction was diluted with ethyl acetate, dried over $MgSO_4$, and then filtered. The solvent was removed in vacuo to give the crude.

The crude was purified on the ISCO (25 g silica, applied with DCM, eluted with 10-15% ethyl acetate/hexane over 5 min) to give t-butyl 6-[(t-butyldimethylsilyl)oxy]-2-{2-fluoro-6-[(3R)-3-methoxypiperidin-1-yl]pyridin-3-yl}-1H-indole-1-carboxylate (201 mg foam, yield 73%, HPLC Rf 4.84 min, MS m/z (M+1) 556.3, TLC 20% ethyl acetate/hexane Rf 0.25).

Step (iv) t-Butyl 2-{2-fluoro-6-[(3R)-3-methoxypiperidin-1-yl]pyridin-3-yl}-6-hydroxy-1H-indole-1-carboxylate

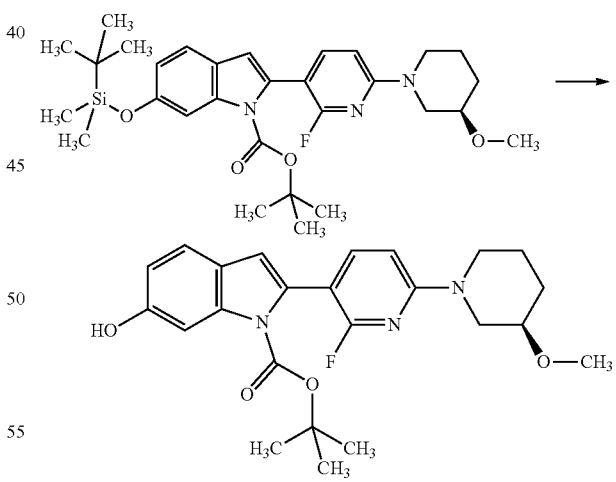

t-Butyl 6-[(t-butyldimethylsilyl)oxy]-2-{2-fluoro-6-[(3R)-3-methoxypiperidin-1-yl]pyridin-3-yl}-1H-indole-1-carboxylate (201 mg, 0.36 mmol) was dissolved in THF (5 ml), cooled on an ice-bath and a 1 M TBAF solution (400 µl, 1.1 eq) was added. The reaction was stirred for 10 min at 0° C.

The reaction was diluted with ethyl acetate, treated with brine, dried over $MgSO_4$, and then filtered. The solvent was removed in vacuo to give the crude.

The crude was purified on the ISCO (12 g silica, applied with DCM, eluted with 20-35% ethyl acetate/hexane over 4 min) to give t-butyl 2-{2-fluoro-6-[(3R)-3-methoxypiperidin-1-yl]pyridin-3-yl}-6-hydroxy-1H-indole-1-carboxylate (159 mg film, HPLC 3.63 min, MS m/z (M+1) 442.2, (M-1) 440.2, 99% yield, TLC Rf 30% ethyl acetate/hexane Rf 0.16).

Step (v) 2-{2-Fluoro-6-[(3R)-3-methoxypiperidin-1-yl]pyridin-3-yl}-1H-indol-6-ol

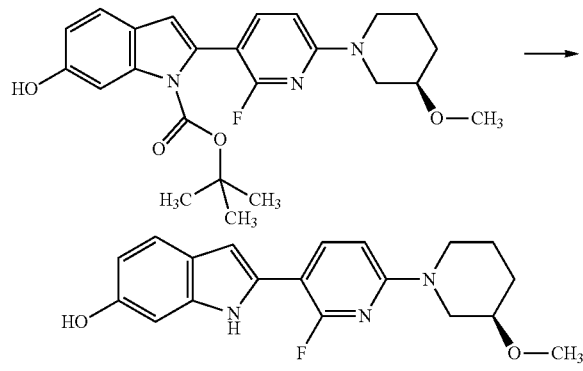

In a 5 ml microwave vial, t-butyl 2-{2-fluoro-6-[(3R)-3-methoxypiperidin-1-yl]pyridin-3-yl}-6-hydroxy-1H-indole-1-carboxylate (159 mg, 0.36 mml) was dissolved in methanol (3 ml). The reaction was subjected to the microwave for 60 min at 150° C.

A few drops of water was added to the clear solution and a solid was obtained with a stream of $N_2$ to give 2-{2-fluoro-6-[(3R)-3-methoxypiperidin-1-yl]pyridin-3-yl}-1H-indol-6-ol (82 mg solid, HPLC 3.02 min, MS m/z (M+1) 342.3, (M-1) 340.2, 67% yield, TLC Rf 30% ethyl acetate/hexane Rf 0.16).

Example Compound 5: 2-{2-Fluoro-6-[3-methoxypiperidin-1-yl]pyridin-3-yl}-1H-indol-5-ol

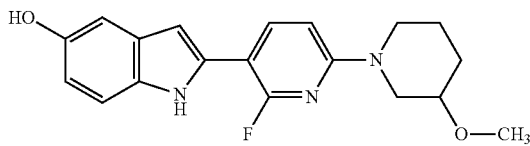 [SMILES: COC1CCCN(c2ccc(-c3cc4cc(O)ccc4[nH]3)c(F)n2)C1]

Step (i) 2-Fluoro-6-[3-methoxypiperidin-1-yl]pyridine

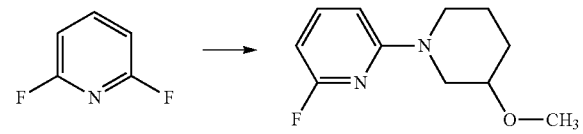

3-Methoxypiperidine (1.1 g, 9.4 mmol) was dissolved in dioxane (8 ml) and 2,6-difluoropyridine (0.95 ml, 1.1 eq) was added followed by Hunig's base (2.4 ml, 1.5 eq). The reaction was heated to 100° C. for 4 h.

The cooled reaction mixture was taken into ethyl acetate, washed with water, treated with brine, dried over $MgSO_4$ and then filtered. The solvent was removed in vacuo to give the crude oil.

The crude oil was purified on the ISCO (40 g silica, applied with hexane, eluted with 5-20% ethyl acetate/hexane over 5 min) to give 2-fluoro-6-[3-methoxypiperidin-1-yl]pyridine (1.29 g oil, HPLC Rf 2.85 min, 76% yield, MS m/z (M+1) 211.0 (very weak), TLC 10% ethyl acetate/hexane Rf 0.14)

Step (ii) 3-Bromo-2-fluoro-6-[3-methoxypiperidin-1-yl]pyridine

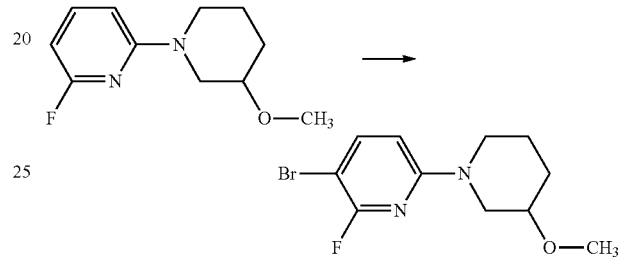

2-Fluoro-6-[3-methoxypiperidin-1-yl]pyridine (1.2 g, 6.1 mmol) was dissolved in acetonitrile (25 ml), cooled on an ice-bath and NBS (1.1 g, 1 eq) was added in 2 portions. The reaction was allowed to stir at 0° C. for 5 min then stirred at rt for 30 min.

Diethyl ether was added to the mixture, the solution was washed with water, treated with brine, dried over $MgSO_4$ and then filtered. The solvent was removed in vacuo to give the crude.

The crude was purified on the ISCO (40 g silica, applied with hexane/DCM, eluted with 5-15% ethyl acetate/hexane over 3 min) to give 3-bromo-2-fluoro-6-[3-methoxypiperidin-1-yl]pyridine (1.62 g oil, HPLC Rf 3.31 min, 92% yield, MS m/z (M+1) 288.9, 290.9, TLC 20% ethyl acetate/hexane Rf 0.19).

Step (iii) t-Butyl 5-[(t-butyldimethylsilyl)oxy]-2-{2-fluoro-6-[3-methoxypiperidin-1-yl]pyridin-3-yl}-1H-indole-1-carboxylate

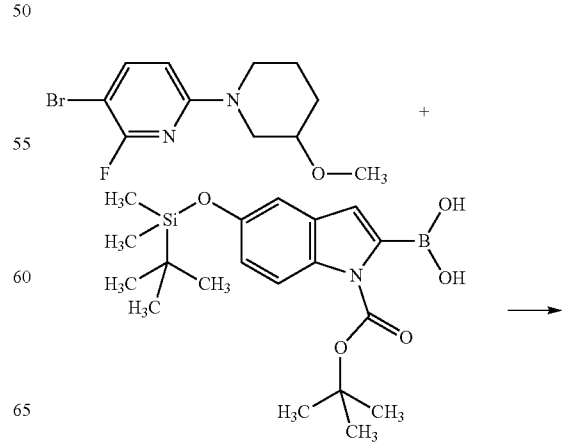

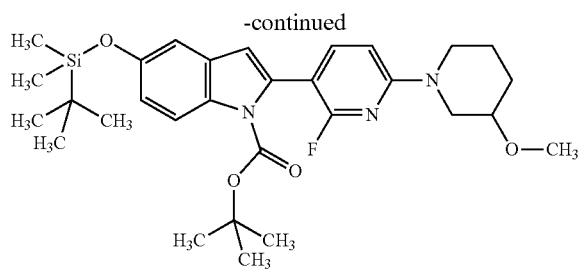

3-Bromo-2-fluoro-6-[3-methoxypiperidin-1-yl]pyridine (145 mg, 0.5 mmol) and {1-[(t-butoxy)carbonyl]-5-[(t-butyldimethylsilyl)oxy]-1H-indol-2-yl}boronic acid (235 mg, 1.2 eq) were dissolved in dioxane (3 ml) in a 5 ml microwave vial. The solution was bubbled with $N_2$ for 1.5 min, then Pd(dppf)$Cl_2$ DCM (20 mg, 5 mol %) was added followed by 2 M $K_2CO_3$ (0.75 ml, 3 eq). The solution was again bubbled with $N_2$ for 5 min, capped then put in a pre-heated oil bath. The reaction was heated to 90° C. for 1 h.

The aqueous fraction was removed from the cooled reaction, and the organic fraction was diluted with ethyl acetate, dried over $MgSO_4$ and then filtered. The solvent was removed in vacuo to give the crude.

The crude was purified on the ISCO (25 g silica, applied with DCM, eluted with 5-15% ethyl acetate/hexane over 6 min) to give t-butyl 5-[(t-butyldimethylsilyl)oxy]-2-{2-fluoro-6-[3-methoxypiperidin-1-yl]pyridin-3-yl}-1H-indole-1-carboxylate (260 mg foam, 94% yield, HPLC Rf 4.42 min, MS m/z (M+1) 556.3, TLC 20% ethyl acetate/hexane Rf 0.22).

Step (iv) t-Butyl 2-{2-fluoro-6-[3-methoxypiperidin-1-yl]pyridin-3-yl}-5-hydroxy-1H-indole-1-carboxylate

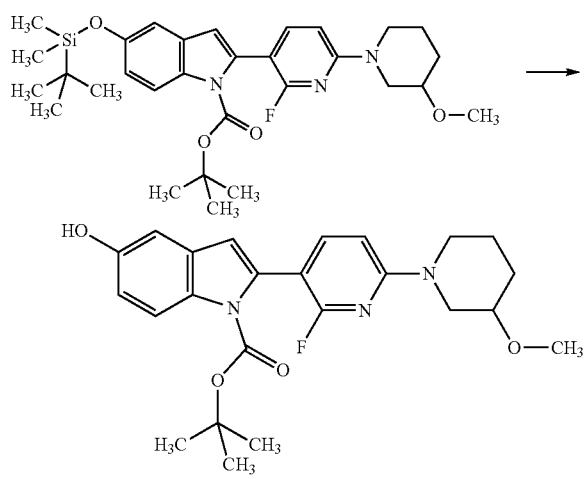

t-Butyl 5-[(t-butyldimethylsilyl)oxy]-2-{2-fluoro-6-[3-methoxypiperidin-1-yl]pyridin-3-yl}-1H-indole-1-carboxylate (260 mg, 0.47 mmol) was dissolved in THF (7 ml), cooled on an ice-bath and a 1 M TBAF solution (0.51 ml, 1.1 eq) was added. The reaction stirred 10 min at 0° C.

The reaction was diluted with ethyl acetate, treated with brine, dried over $MgSO_4$ and then filtered. The solvent was removed in vacuo to give the crude.

The crude was purified on the ISCO (12 g silica, applied with DCM, eluted with 20-35% ethyl acetate/hexane over 5 min) to give t-butyl 2-{2-fluoro-6-[3-methoxypiperidin-1-yl]pyridin-3-yl}-5-hydroxy-1H-indole-1-carboxylate (204 mg oil, HPLC 3.46 min, MS m/z (M+1) 442.1, (M-1) 440.2, 99% yield, TLC Rf 50% ethyl acetate/hexane Rf 0.49).

Step (v) 2-{2-Fluoro-6-[3-methoxypiperidin-1-yl]pyridin-3-yl}-1H-indol-5-ol

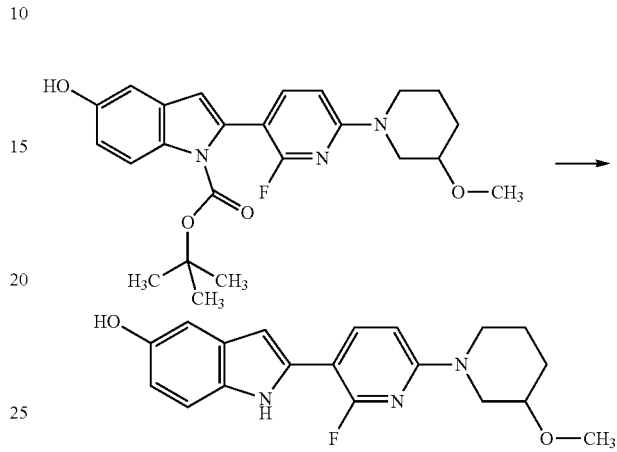

In a 5 ml microwave vial, t-butyl 2-{2-fluoro-6-[3-methoxypiperidin-1-yl]pyridin-3-yl}-5-hydroxy-1H-indole-1-carboxylate (204 mg, 0.46 mml) was dissolved in methanol (5 ml). The reaction was subjected to the microwave for 90 min at 150° C.

A solid crystallized from the solution, which was filtered off to give 2-{2-fluoro-6-[3-methoxypiperidin-1-yl]pyridin-3-yl}-1H-indol-5-ol (55 mg solid, HPLC 2.90 min, MS m/z (M+1) 342.1, (M-1) 340.0, 35% yield).

Example Compound 6: 2-{2-Fluoro-6-[(3S)-3-($^3H_3$)methoxypiperidin-1-yl]pyridin-3-yl}-1H-indol-5-ol

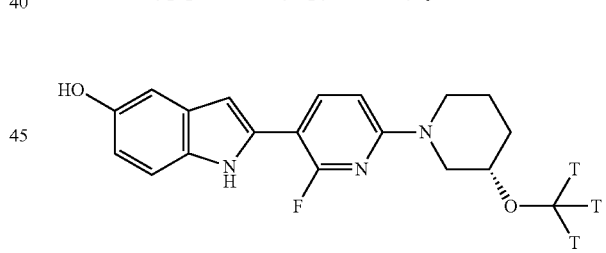

Step (i) t-Butyl 5-hydroxy-2-{6-[(3S)-3-methoxypiperidin-1-yl]-2-nitropyridin-3-yl}-1H-indole-1-carboxylate

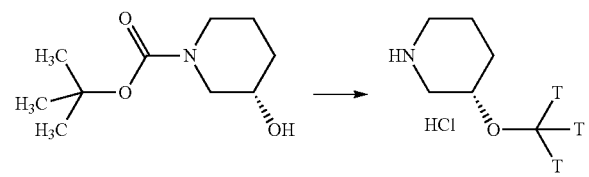

To t-butyl (3S)-3-hydroxypiperidine-1-carboxylate (2.1 mg, 10.4 µmol), dissolved in DMF (0.5 ml), a 60% paraffin dispersion of sodium hydride (spatula tip) was added, and the reaction stirred for 20 min at rt. To the solution iodo ($^3$H$_3$)methane (74 mCi) dissolved in DMF (0.2 ml) was added, and the reaction stirred overnight.

The reaction was quenched with an ammonium chloride solution, extracted with ethyl acetate, dried with sodium sulfate, filtered and the solvent was removed by a stream of N$_2$.

The intermediate was purified on a silica column (Pasteur pipette), eluted with ethyl acetate/hexane 1:3 and the fractions containing activity were collected, and the solvent was removed by a stream of N$_2$.

The product was dissolved in dioxane (0.5 ml), cooled on an ice-bath and 4 M HCl in dioxane (0.5 ml) was added. The reaction was stirred for 1 h at rt, and then stirred at 45° C. for 30 min. The solvent was removed by a stream of N$_2$ to give (3S)-3-($^3$H$_3$) methoxypiperidine HCl that was used as is in the next reaction.

Step (ii) 2-{2-Fluoro-4-[(3S)-3-($^3$H$_3$)methoxypiperidin-1-yl]phenyl}-1H-indol-5-ol

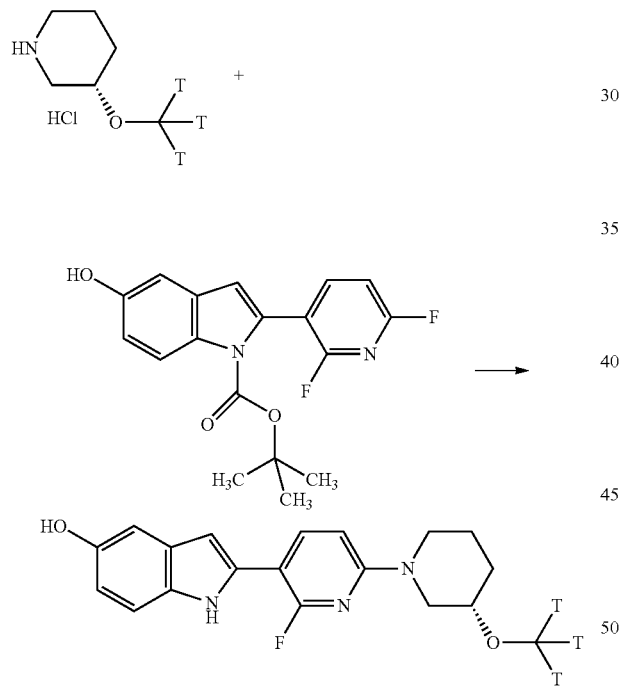

(3S)-3-($^3$H$_3$)Methoxypiperidine HCl (from the above reaction) was dissolved in methanol (0.5 ml). To that solution, t-butyl 2-(2,6-difluoropyridin-3-yl)-5-hydroxy-1H-indole-1-carboxylate (3.8 mg, 11 μmol, see WO2021074351 A1 for method of manufacture) and Hunig's base (10 μl, excess) was added and the reaction was subjected to the microwave for 60 min at 150° C.

The cooled reaction was evaporated and the remains were purified on an HPLC (Kromasil C18, 250×10 mm eluting with 70% acetonitrile in 0.1% TFA) to give 2-{2-fluoro-4-[(3S)-3-($^3$H$_3$)methoxypiperidin-1-yl]phenyl}-1H-indol-5-ol (radiochemical concentration 71 MBq (1.9 mCi), molar activity 2.61 TBq/mmol (70 Ci, mmol), MS m/z (M+1) 348).

Example Compound 7: 2-[2-($^{18}$F)Fluoro-6-[(3S)-3-methoxypiperidin-1-yl]pyridin-3-yl]-1H-indol-5-ol

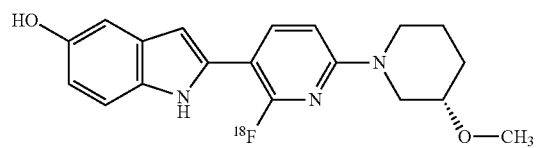

Step (i) 2-[(3S)-3-Methoxypiperidin-1-yl]-6-nitropyridine

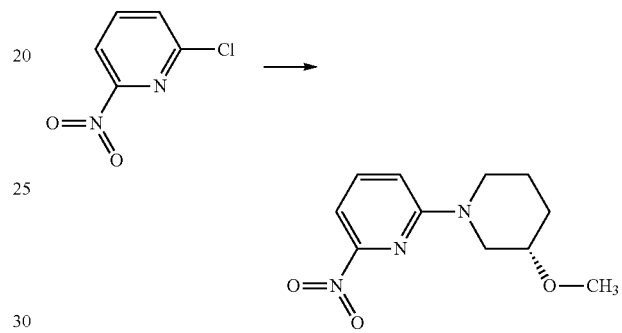

2-Chloro-6-nitropyridine (0.63 g, 4 mmol) and (S)-3-methoxypiperidine HCl (0.9 g, 1.5 eq) were slurried in dioxane (6 ml) followed by the addition of Hunig's base (2.9 ml, 1.5 eq). The reaction was heated to 100° C. for 19 h.

The cooled reaction mixture was taken into ethyl acetate, washed with water, treated with brine, dried over MgSO$_4$ and filtered. The solvent was removed in vacuo to give the crude oil.

The crude was purified on the ISCO (40 g silica, applied with hexane, eluted with 15-30% ethyl acetate/hexane over 8 min) to give 2-[(3S)-3-methoxypiperidin-1-yl]-6-nitropyridine (0.63 g oil, HPLC Rf 2.91 min, 67% yield, MS m/z (M+1) 238.2 (very weak), TLC 30% ethyl acetate/hexane Rf 0.22).

Step (ii) 3-Bromo-6-[(3S)-3-methoxypiperidin-1-yl]-2-nitropyridine

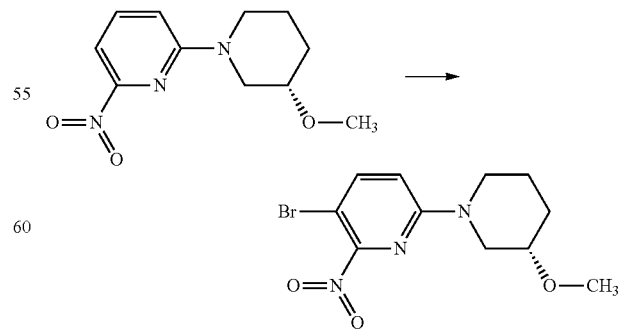

2-[(3S)-3-Methoxypiperidin-1-yl]-6-nitropyridine (0.61 g, 2.6 mmol) was dissolved in acetonitrile (15 ml), cooled on an ice-bath and NBS (0.65 g, 1 eq) was added. The reaction was allowed to stir at 0° C. for 5 min then stirred at rt for 60 min.

The reaction was taken into ethyl acetate, treated with brine twice, dried over MgSO₄ and filtered. The solvent was removed in vacuo to give the crude.

The crude was purified on the ISCO (40 g silica, applied with hexane/DCM, eluted with 15-30% ethyl acetate/hexane over 6 min) to give 3-bromo-6-[(3S)-3-methoxypiperidin-1-yl]-2-nitropyridine (0.74 g oil, HPLC Rf 3.27 min, 91% yield, MS m/z (M+1) 316.0, 318.0, TLC 60% ethyl acetate/hexane Rf 0.30).

Step (iii) t-Butyl 5-[(t-butyldimethylsilyl)oxy]-2-{6-[(3S)-3-methoxypiperidin-1-yl]-2-nitropyridin-3-yl}-1H-indole-1-carboxylate

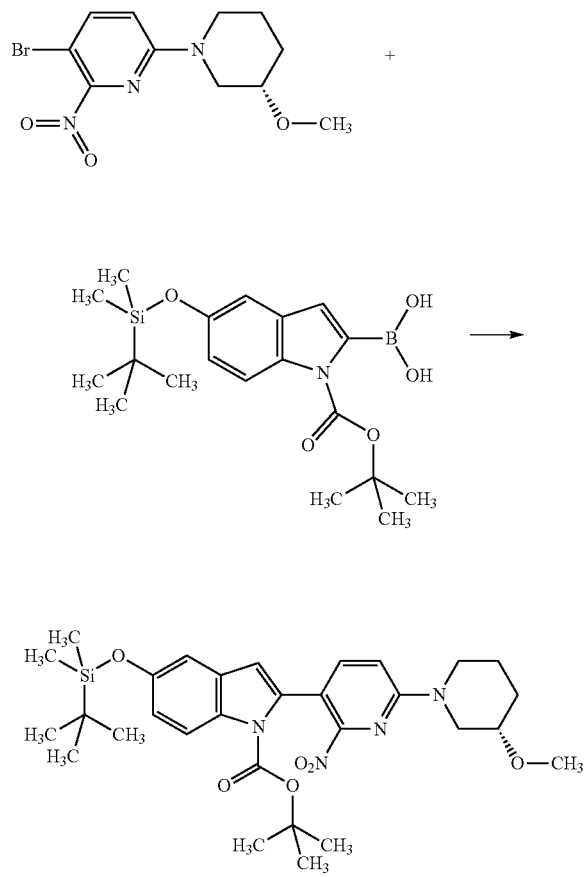

3-Bromo-6-[(3S)-3-methoxypiperidin-1-yl]-2-nitropyridine (316 mg, 1 mmol) and {1-[(t-butoxy)carbonyl]-5-[(t-butyldimethylsilyl)oxy]-1H-indol-2-yl}boronic acid (550 mg, 1.4 eq) were dissolved in dioxane (6 ml) in a 20 ml microwave vial. The solution was bubbled with N₂ for 2 min, then Pd(dppf)Cl₂ DCM (41 mg, 5 mol %) was added followed by 2 M K₂CO₃ (31.5 ml, 3 eq). The solution was again bubbled with N₂ for 5 min, capped then put in a pre-heated oil bath. The reaction was run at 90° C. for 1 h.

The aqueous phase was removed from the cooled reaction mixture, and then the reaction mixture was diluted with ethyl acetate, dried over MgSO₄ and filtered. The solvent was removed in vacuo to give the crude.

The crude was purified on the ISCO (40 g silica, applied with DCM, eluted with 10-20% ethyl acetate/hexane over 6 min) to give t-butyl 5-[(t-butyldimethylsilyl)oxy]-2-{6-[(3S)-3-methoxypiperidin-1-yl]-2-nitropyridin-3-yl}-1H-indole-1-carboxylate (334 mg foam, 57% yield, HPLC Rf 4.37 min, MS m/z (M+1) 583.4, TLC 20% ethyl acetate/hexane Rf 0.16, ¹H NMR (400 MHz, CDCl₃) δ 7.70 (d, J=9.0 Hz, 1H), 6.72 (d, J=9.0 Hz, 1H), 3.85 (ddt, J=13.2, 3.4, 1.1 Hz, 1H), 3.68 (ddd, J=13.3, 6.6, 3.8 Hz, 1H), 3.52-3.31 (m, 6H), 2.05-1.94 (m, 1H), 1.88 (ddp, J=14.2, 7.3, 3.6 Hz, 1H), 1.69 (ddt, J=12.8, 8.7, 3.9 Hz, 1H), 1.61-1.48 (m, 1H).

¹³C NMR (101 MHz, CDCl₃) δ 156.28, 144.12, 110.93, 93.14, 77.36, 77.04, 76.73, 74.58, 56.40, 48.46, 45.43, 29.58, 21.80.)

Step (iv) t-Butyl 5-hydroxy-2-{6-[(3S)-3-methoxypiperidin-1-yl]-2-nitropyridin-3-yl}-1H-indole-1-carboxylate

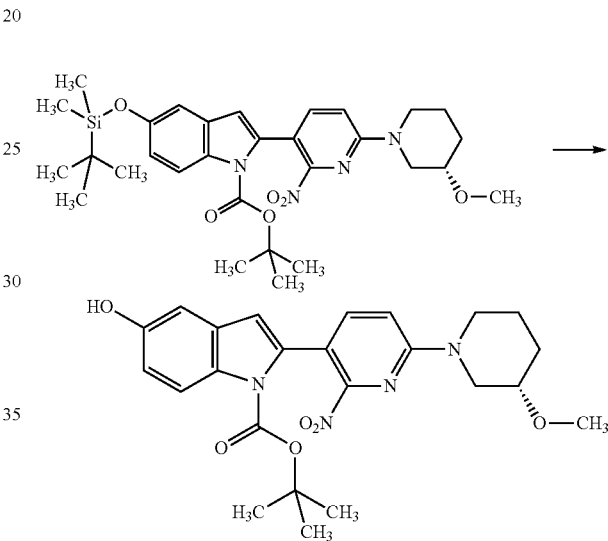

t-Butyl 5-[(t-butyldimethylsilyl)oxy]-2-{6-[(3S)-3-methoxypiperidin-1-yl]-2-nitropyridin-3-yl}-1H-indole-1-carboxylate (236 g, 0.40 mmol) was dissolved in THF (7 ml), cooled on an ice-bath and a 1 M TBAF solution (450 μl, 1.1 eq) was added. The reaction stirred 10 min at 0° C.

The reaction was diluted with ethyl acetate, treated with brine, dried over MgSO₄ and filtered. The solvent was removed in vacuo to give the crude.

The crude was purified on the ISCO (12 g silica, applied with DCM, eluted with 25-40% ethyl acetate/hexane over 5 min) to give t-butyl 5-hydroxy-2-{6-[(3S)-3-methoxypiperidin-1-yl]-2-nitropyridin-3-yl}-1H-indole-1-carboxylate (142 mg film, HPLC 3.43 min, MS m/z (M+1) 469.3, (M-1) 467.3, 75% yield, TLC Rf 40% ethyl acetate/hexane Rf 0.16, ¹H NMR (400 MHz, CDCl₃) δ 8.03 (d, J=8.9 Hz, 1H), 7.56 (d, J=8.6 Hz, 1H), 6.91 (d, J=2.5 Hz, 1H), 6.88-6.81 (m, 2H), 6.35 (d, J=0.7 Hz, 1H), 3.95 (dd, J=13.3, 3.3 Hz, 1H), 3.76 (ddd, J=13.4, 6.5, 3.8 Hz, 1H), 3.56 (dd, J=13.3, 7.2 Hz, 1H), 3.42 (s, 4H), 3.37 (tt, J=7.2, 3.5 Hz, 1H), 2.00 (dq, J=11.6, 3.6 Hz, 1H), 1.88 (dtt, J=13.9, 7.1, 3.6 Hz, 1H), 1.69 (dtd, J=12.5, 8.2, 3.7 Hz, 1H), 1.55 (ddt, J=15.2, 8.8, 4.1 Hz, 1H), 1.39 (s, 9H).

¹³C NMR (101 MHz, CDCl₃) δ 156.82, 151.78, 149.82, 142.77, 134.69, 131.55, 130.02, 116.72, 113.52, 111.46, 110.10, 109.35, 105.52, 83.70, 77.36, 77.04, 76.72, 74.81, 56.41, 48.38, 45.46, 29.85, 27.80, 21.99.)

Step (v) 2-[2-($^{18}$F)fluoro-6-[(3S)-3-methoxypiperidin-1-yl]pyridin-3-yl]-1H-indol-5-ol

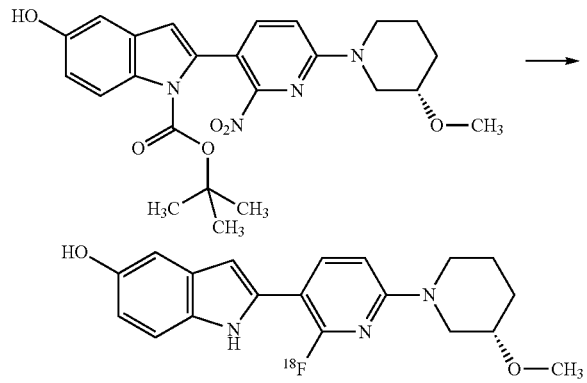

Non-carrier added [$^{18}$F]F$^-$ was produced via the $^{18}$O(p, n)$^{18}$F reaction (Scanditronix MC-17 cyclotron) and transferred in [$^{18}$O]water to an automated radio-synthesizer (GE Tracerlab FX2N) in a lead shielded hotcell. The [$^{18}$F]F$^-$ was trapped on a PS—HCO$_3$ ion exchange column (Chromafix) before being eluted with K$_2$CO$_3$ (1.37 mg, 10 μmol) and Kryptofix 2.2.2 (14 mg, 5 μmol) in water/methanol (10/90, 1 mL) into the reaction vessel. Solvents were evaporated under vacuum and subsequently azeotropically dried with acetonitrile (1 mL) under continuous nitrogen flow. The precursor, tert-butyl (S)-5-hydroxy-2-(6-(3-methoxypiperidin-1-yl)-2-nitropyridin-3-yl)-1H-indole-1-carboxylate (3 mg, 6.4 μmol), in DMSO (1 mL) was added and the reactor was heated to 160° C. for 20 min. The reactor was cooled down to 70° C. and methanol (2 mL) was added before heating to 130° C. for 20 min. The reactor was then cooled to 50° C. and the reaction mixture was diluted with acetonitrile:water (20:80) before being injected onto a reverse phase HPLC column (LUNA 10 μm C18(2) 100 Å, 250 mm×10 mm, Phenomenex). The 2-[2-($^{18}$F)fluoro-6-[(3S)-3-methoxypiperidin-1-yl]pyridin-3-yl]-1H-indol-5-ol was eluted with a mobile phase of acetonitrile-NH$_4$CO$_2$H$_{aq}$ (0.05 M) (45/55, v/v) at a flow rate of 5 mL/min. The retention time of 2-[2-($^{18}$F)fluoro-6-[(3S)-3-methoxypiperidin-1-yl]pyridin-3-yl]-1H-indol-5-ol was 14-16 min. The collected fraction was diluted with water (20 mL) and loaded onto a solid phase extraction (SPE) column (SepPak tC18, Waters). The SPE column was washed with water (10 mL) before the 2-[2-($^{18}$F)fluoro-6-[(3S)-3-methoxypiperidin-1-yl]pyridin-3-yl]-1H-indol-5-ol was eluted by ethanol (1 mL) and mixed with sterile saline (9 mL). The purity and molar activity were determined by reverse-phase HPLC (InfinityLab Poroshell 120 PFP, 4.6×150 mm, 2.7 μm, Agilent) with UV and gamma detector connected in series. 2-[2-($^{18}$F)fluoro-6-[(3S)-3-methoxypiperidin-1-yl]pyridin-3-yl]-1H-indol-5-ol was eluted with acetonitrile-NH$_4$CO$_2$H (0.05 M) (50/50, v/v) at a flow rate of 3 mL/min (retention time=4.3-4.5 min). Radiochemical identity was confirmed by co-injection of the authentic sample of 2-{2-fluoro-6-[(3S)-3-methoxypiperidin-1-yl]pyridin-3-yl}-1H-indol-5-ol (Example Compound 1).

A summary of the structure of example compounds 1 to 7, and the C Log P of the compounds, is provided below in Table 1.

TABLE 1

| Example Compound No. | Structure | CLogP |
|---|---|---|
| 1 | 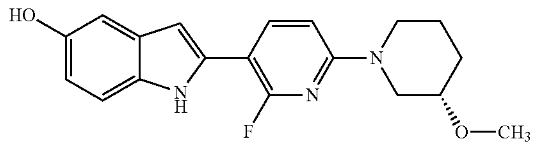 | 3.8 |
| 2 | 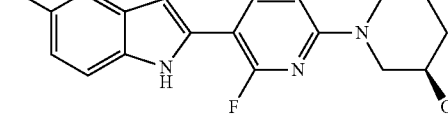 | 3.8 |
| 3 | 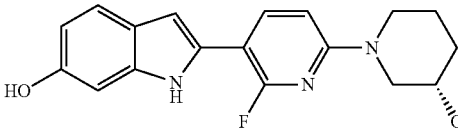 | 3.8 |
| 4 | 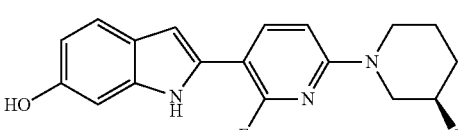 | 3.8 |

TABLE 1-continued

| Example Compound No. | Structure | CLogP |
|---|---|---|
| 5 | HO-indole-pyridine(F)-piperidine-O-CH3 | 3.8 |
| 6 | HO-indole-pyridine(F)-piperidine-O-C($^3$H)$_3$ | 3.8 |
| 7 | HO-indole-pyridine($^{18}$F)-piperidine-O-CH3 | 3.8 |

BIOLOGICAL TESTING

Example (a): Biological Assay Methods and Results $^3$H-THK5117 Competition Binding to Tau Fibrils In Vitro Preparation of recombinant 0N4R Tau fibrils was performed as previously described in Morozova, O. A., Biochemistry (2013), Vol., 52(40), pages 6960-6967. Competition binding experiments to 0N4R Tau fibrils were performed by incubating increasing concentrations [$10^{-10}$-$10^{-6}$ M] of the Example compounds of the invention, or the known tau specific ligand PBB3 (PBB3 was synthesized as previously described in M. Maruyama, et al, Neuron 2013, 79, 1094-1108) or MK6240 (Novandi Chemistry AB), in the presence of 3 nM of the known tau ligand [$^3$H]-THK5117 (Novandi Chemistry) and 0.2 mM 0N4R tau fibrils in binding buffer (50 mM Tris-HCl, pH 7.4, 0.1% BSA) for 1 h in the dark, and at 22° C. The incubation was terminated by filtration through a Whatman GF/B glass filter (Whatman International, Kent, UK) using a Brandel cell harvester. The filter was then washed rapidly four times with 3 mL of ice-cold wash buffer (5 mM Tris-HCl, 0.25 mM NaCl, 5% EtOH), and equilibrated for 1 h in scintillation vials containing 5 mL of Ultima Gold scintillation fluid before being analysed using a Liquid Scintillation Analyzer.

The results are shown in Table 2 in the column labeled "Tau IC$_{50}$". For compounds that were run in the competition binding experiment more than once, the Tau IC$_{50}$ value in Table 2 is the average of the results of each experiment.

Biological Assay Results

TABLE 2

| Example Compound No. | Tau IC$_{50}$ (nM) |
|---|---|
| 1 | 1.7 |
| 2 | 31.8 |
| 3 | n.d |
| 4 | n.d |
| 5 | n.d |
| 6 | n.d | n.d = not determined.

The results in Table 2 show that the Example compounds of the invention have high affinity binding to recombinant 4R tau fibrils.

Example (b): Example Compound 1 and Comparative Example Compound 1 Mouse Intravenous (IV) Pharmacokinetic Study with Bioanalysis A pharmacokinetic study of plasma and brain exposure in mice after IV administration of Example Compound 1 or Comparative Example Compound 1 was carried out following the protocol described in Loryan, I., et al, Pharm Res (2014) 31: 2203-2219. Comparative Example Compound 1 is 2-{2-Fluoro-6-[4-(hydroxymethyl)piperidin-1-yl]pyridin-3-yl}-1H-indol-5-ol, and has the following structure:

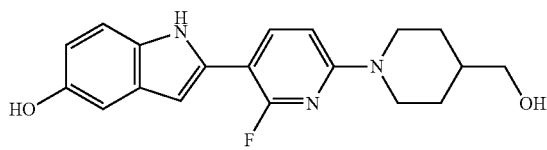 [SMILES: OCC1CCN(c2ccc(-c3cc4cc(O)ccc4[nH]3)c(F)n2)CC1]

Comparative Example Compound 1 is Example Compound No. 48 disclosed in WO2019/197502 A1 and was synthesized as described in that document.

Experimental Protocol and Bioanalysis

The experimental protocol and bioanalysis described in Loryan, I., et al, Pharm Res (2014) 31: 2203-2219 was followed to measure mouse plasma and brain exposure. Table 3 below provides specific details of the mice, sampling, dose, formulation, method and additional information regarding the experiment, and Table 4 below provides further information regarding the sampling in the experiment. As can be seen from Table 4, n=3 mice per time point.

TABLE 3

| | | |
|---|---|---|
| Animal Information | Species/Strain/Sex | Mouse/NMRI/male |
| | Weight | Approximately 20-25 g (all animals weighed prior to dosing). |
| | Housing & Husbandry | Group/singly housed as appropriate in the animal facility and maintained under a 12 h light/dark cycle with free access to food and water, and temperature and humidity controlled according to Home Office regulations. |
| | Surgical Preparation | N/A |
| | Dose Groups & n= | n = 12 per dose route |
| | Fed/Fasted Status | Fed |
| Dosing and Formulation Information | Dosing route | Intravenous |
| | Dose Level | 1 mg/kg |
| | Dose Concentration | 0.2 mg/kg |
| | Dose Volume | 5 mL/kg |
| | Formulation | Solution in HP-β-CD (20% w/v) in Saline |
| Sampling Information | Serial/Terminal Occasions | Serial/Terminal Day 1 only |
| | Sample(s) | IV Leg Serial/terminal sampling of whole blood for plasma at 5 time point(s) (n = 3 per time point). |
| | Time-points (h) | IV Leg Plasma: 2 min, 10 min, 30 min, 60 min, & 120 min post dose Brain: 2 min, 10 min, 60 min, & 120 min post dose |
| Method | | Serial/terminal blood samples from animals were collected as specified in Table 4 below and delivered into labelled polypropylene tubes containing anticoagulant (heparin) and held on wet ice for a maximum of 30 minutes. The blood samples were then be centrifuged for plasma (4° C., 21100 g for 5 min) and the resulting plasma transferred into labelled safe-lock Eppendorf 1.5 mL clear tubes. All samples were stored immediately after collection at ≤−20° C. prior to transfer to storage at <−70° C. pending bioanalysis. Appropriate matrix samples were also provided for bioanalytical purposes. Perfused brain samples were snap frozen upon collection in corresponding pre-weighed labelled tube and immediately transferred to storage at <−70° C. pending bioanalysis. |
| Sample Preparation and Analysis | Sample preparation | Protein precipitation with acetonitrile |
| | Sample analysis | UHPLC - tandem mass spectrometry using electrospray ionisation. |
| Additional Information | Clinical Signs | All animals: ill health/overt toxicity monitored |
| | Post-Dosing Observations | Not required |

TABLE 4

| Animal Number | IV Sampling Time Points | | | | |
|---|---|---|---|---|---|
| | 2 min | 10 min | 30 min | 60 min | 120 min |
| 1 | X | | | | |
| 2 | X | | | | |
| 3 | X | | | | |
| 4 | | X | | | |
| 5 | | X | | | |
| 6 | | X | | | |
| 7 | | | X | | |
| 8 | | | X | | |
| 9 | | | X | | |
| 10 | | | | x | X |
| 11 | | | | x | X |
| 12 | | | | x | X | x - Serial sample whole blood for plasma via tail vein
X - Terminal sample whole blood for plasma via tail vein, and brain sample in addition.

Results

No adverse events were observed in the mice during the study. Table 5 and 6 below show a summary of the pharmacokinetic (PK) parameters measured for Example Compound 1 in plasma (Table 5) and brain (Table 6) following IV administration of Example Compound 1 at 1 mg/kg (mean, n=3).

TABLE 5

| PK Parameter | Units | Result |
|---|---|---|
| $t_{1/2}$ | hr | 0.4 |
| $T_{max}$ | hr | 0.03 |
| $C_{max}$ | ng/mL | 781.7 |
| $AUC_{last}$ | hr * ng/mL | 263.5 |
| $AUC_{inf}$ | hr * ng/mL | 267.1 |
| Cl | mL/min/kg | 62.4 |
| Vd | L/kg | 1.2 |
| MRT | hr | 0.3 |
| $C_0$ | ng/mL | 883.8 |

TABLE 6

| PK Parameter | Units | Result |
|---|---|---|
| $t_{1/2}$ | hr | 0.3 |
| $T_{max}$ | hr | 0.03 |

TABLE 6-continued

| PK Parameter | Units | Result |
|---|---|---|
| $C_{max}$ | ng/g | 1186.7 |
| $AUC_{last}$ | hr * ng/g | 454.6 |
| $AUC_{inf}$ | hr * ng/g | 457.8 |

Table 7 below shows the AUC in brain and plasma for total and unbound concentrations of Example Compound 1 and Comparative Example Compound 1, and corresponding brain:plasma ratios of each compound.

TABLE 7

| | | Total concentration | | Unbound concentration | |
|---|---|---|---|---|---|
| | | AUC hr * ng/g | brain:plasma ratio | AUC hr * ng/g | brain:plasma ratio |
| Example Compound 1 | Plasma | 267.1 | 1.7 | 0.16 | 0.56 |
| | Brain | 457.8 | | 0.09 | |
| Comparative Example Compound 1 | Plasma | 151 | 0.1 | 14 | 0.002 |
| | Brain | 15 | | 0.030 | |

The total concentration vs. time profiles in plasma and in brain following IV administration of Example Compound 1 are shown in FIG. 1.

The data show that Example Compound 1 readily enters the brain following IV dosing and is eliminated with an elimination half-life of about 0.3 hours.

The total concentration and unbound concentration brain:plasma ratios show that for Comparative Example Compound 1 the ability of that compound to penetrate the brain is limited as the unbound AUC in brain is only about 0.2% of the corresponding plasma AUC.

In contrast, the unbound AUC for Example Compound 1 in brain is about 56% of the plasma AUC. This shows that Example Compound 1 has good brain penetration.

The invention claimed is:

1. A compound of formula (I)

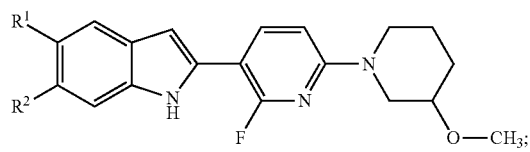

(I)

or a pharmaceutically acceptable salt thereof, wherein either:
$R^1$ is OH, and $R^2$ is H; or
$R^1$ is H, and $R^2$ is OH.

2. A compound of claim 1, of formula (Ia) or (Ib):

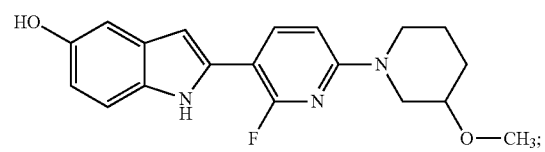

(Ia)

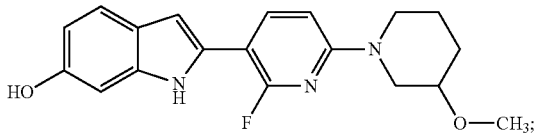

(Ib)

or a pharmaceutically acceptable salt thereof.

3. A compound of claim 1, of formula (Ia):

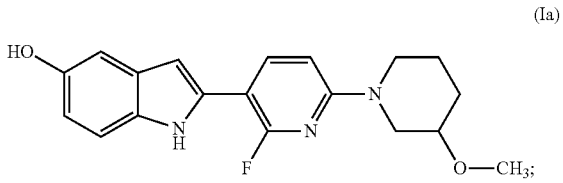 [SMILES: COC1CCCN(c2ccc(-c3cc4cc(O)ccc4[nH]3)c(F)n2)C1]

(Ia)

or a pharmaceutically acceptable salt thereof.

4. A compound of claim 1, selected from the group consisting of:

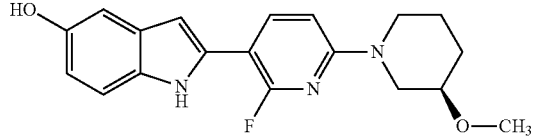

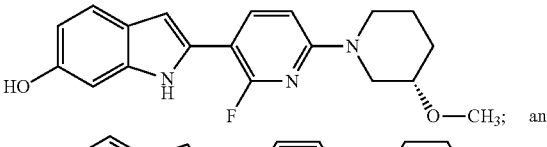

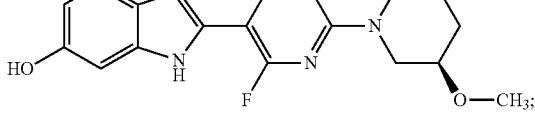

or a pharmaceutically acceptable salt thereof.

5. A compound of claim 1, which is:

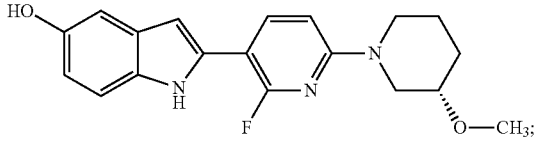

or a pharmaceutically acceptable salt thereof.

6. A compound of claim 1, or a pharmaceutically acceptable salt thereof, wherein the compound comprises a radioisotope comprising $^3H$, $^{11}C$, $^{13}C$, $^{14}C$, $^{13}N$, $^{15}O$, $^{18}F$ $^{19}F$, or a combination thereof.

7. A compound of claim 6, or a pharmaceutically acceptable salt thereof, wherein the compound comprises a radioisotope comprising $^{18}F$, $^3H$, $^{11}C$, or a combination thereof.

8. A compound selected from the group consisting of:

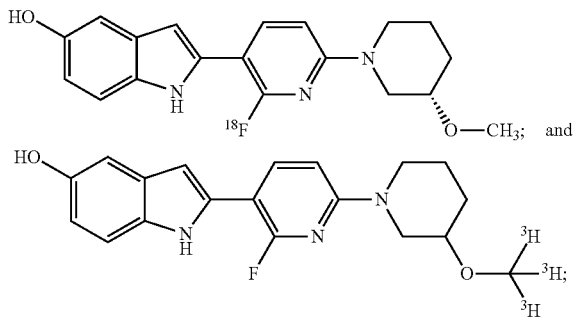

or a pharmaceutically acceptable salt thereof.

9. A compound which is:

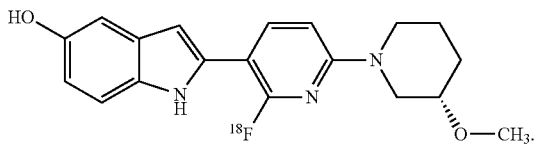

10. A pharmaceutical composition comprising a compound of claim 1 and a pharmaceutically suitable carrier.

11. A pharmaceutical composition comprising a compound of claim 9 and a pharmaceutically suitable carrier.

12. The pharmaceutical composition of claim 10, wherein the composition contains an additional active ingredient.

13. The pharmaceutical composition of claim 10, wherein the additional active ingredient is an additional therapeutic agent or a diagnostic agent.

14. A method of diagnosing or monitoring the progression of a disease or a disorder in a subject in need thereof, the method comprising administering to the subject in need thereof a compound of claim 6, or a pharmaceutically acceptable salt thereof, wherein the disease or disorder comprises Alzheimer's disease, corticobasal degeneration, Pick's disease, progressive supranuclear palsy, Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion-body myositis, chronic traumatic encephalopathy, Down's syndrome, Gerstman-Sträussler-Scheinker syndrome, British dementia, familial Danish dementia, dementia pugiiistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.lle383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Sträussler-Scheinker with tau, mutations in LRRK2, SLC9A6-related mental retardation, white matter tauopathy with globular glial inclusions, or any combination thereof.

15. The method of claim 14, further comprising detecting the compound using positron emission topography.

16. A method of diagnosing or monitoring the progression of a disease or a disorder in a subject in need thereof, the method comprising administering to the subject in need thereof a compound of claim 9, or a pharmaceutically acceptable salt thereof, wherein the disease or disorder comprises Alzheimer's disease, corticobasal degeneration, Pick's disease, progressive supranuclear palsy, Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean Parkinsonism, globular glial tauopathies, ageing-related tau astrogliopathy, Parkinsonism-dementia complex of Guam, Niemann-Pick disease type C, myotonic dystrophy, inclusion-body myositis, chronic traumatic encephalopathy, Down's syndrome, Gerstman-Sträussler-Scheinker syndrome, British dementia, familial Danish dementia, dementia pugiiistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.lle383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Sträussler-Scheinker with tau, mutations in LRRK2, SLC9A6-related mental retardation, white matter tauopathy with globular glial inclusions, or any combination thereof.

17. The method of claim 16, further comprising detecting the compound using positron emission topography.

18. The method of claim 16, wherein the disease or disorder is Alzheimer's disease.

* * * * *